United States Patent [19]

Durette et al.

[11] Patent Number: 5,359,071
[45] Date of Patent: Oct. 25, 1994

[54] 15-SUBSTITUTED 4-AZASTEROIDS

[75] Inventors: Philippe L. Durette, New Providence; Craig K. Esser, Belford; William Hagmann, Westfield; Ihor E. Kopka, Millburn, all of N.J.

[73] Assignee: Merck & Co., Inc., Rahway, N.J.

[21] Appl. No.: 30,508

[22] Filed: Mar. 12, 1993

[51] Int. Cl.$^5$ .................................... A61K 31/535
[52] U.S. Cl. ................................ 546/78; 546/77; 544/125
[58] Field of Search ............... 514/284, 232.8; 546/77, 546/78, 28; 544/125; A61K 31/535

[56] References Cited

U.S. PATENT DOCUMENTS

| | | | |
|---|---|---|---|
| 2,227,876 | 1/1941 | Bolt | 546/77 |
| 3,239,417 | 3/1966 | DiTullio et al. | 546/77 |
| 3,264,301 | 8/1966 | Doorenboos | 546/77 |
| 3,285,918 | 11/1966 | Doorenboos et al. | |
| 4,220,775 | 9/1980 | Rasmusson et al. | 549/39 |
| 4,317,817 | 3/1982 | Blohm et al. | |
| 4,377,584 | 3/1983 | Rasmusson et al. | 546/77 |
| 4,596,812 | 6/1986 | Chidsey III, et al. | 514/256 |
| 4,732,897 | 3/1988 | Cainelli et al. | 514/284 |
| 4,760,071 | 7/1988 | Rasmusson et al. | 546/77 |
| 4,845,104 | 7/1989 | Carlin et al. | 546/77 |
| 4,859,681 | 8/1989 | Rasmusson et al. | 546/77 |
| 4,882,319 | 11/1989 | Holt et al. | |
| 4,888,336 | 12/1989 | Holt et al. | 546/77 |
| 4,910,226 | 3/1990 | Holt et al. | |
| 5,021,575 | 6/1991 | King et al. | 546/77 |
| 5,049,562 | 9/1991 | Rasmusson et al. | 546/77 |
| 5,098,908 | 3/1992 | Steinberg et al. | 546/77 |
| 5,138,063 | 8/1992 | Rasmusson et al. | 546/77 |
| 5,151,429 | 9/1992 | Rasmusson et al. | 546/77 |

FOREIGN PATENT DOCUMENTS

| | | |
|---|---|---|
| 970692 | 7/1975 | Canada . |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 285382 | 10/1988 | European Pat. Off. ............. 546/77 |
| 0289327 | 11/1988 | European Pat. Off. . |

(List continued on next page.)

OTHER PUBLICATIONS

Endo., vol. 91, No. 2, pp. 427–437 (1972) by Neri, et al., "*A Biological Profile of a Non-steroidal Antiandrogen, SCH*, 13521 . . . ".
Back et al, J. Org Chem. vol 54, pp. 1904–1910 (1989).
Stinson, Chem & Eng News, 29 Jun. 1992 pp. 7–8.
Helliker, Wall Street Jour. 7 Jun. 1991 pp. A1, A7.
Gormley et al. Chem. Abstr vol. 118 entry 213352h (1992).

(List continued on next page.)

*Primary Examiner*—Donald G. Daus
*Attorney, Agent, or Firm*—Joanne M. Giesser; Melvin Winokur; Paul D. Matukaitis

[57] ABSTRACT

Compounds of the formula

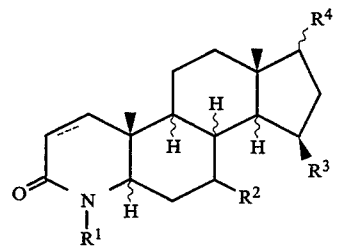

or a pharmaceutically acceptable salt or ester thereof, wherein $R^1$ is selected from the group consisting of hydrogen and $C_{1-10}$ alkyl;

$R^2$ is selected from the group consisting of hydrogen and $C_{1-10}$ alkyl;

$R^3$ is selected from the group consisting of $C_{1-10}$ alkoxyl, $C_{1-10}$ alkyl and cyano;

$R^4$ is selected from the group consisting of $C_{1-10}$ alkenyloxyl, $C_{1-10}$ alkoxyl, $C_{1-10}$ alkyl, $C_{1-10}$ alkylcarbamic, $C_{1-10}$ alkylcarbonyloxyl, carbonyl, hydroxyl, and —$NHR^5$, and $R^5$ is selected from the group consisting of hydrogen and $C_{1-10}$ alkylcarbonyl. Such compounds are useful as selective antagonists of testosterone 5α-reductase 1.

3 Claims, No Drawings

FOREIGN PATENT DOCUMENTS

| | | |
|---|---|---|
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 1465544 | 11/1965 | France . |
| WO91/12261 | 8/1991 | PCT Int'l Appl. . |

OTHER PUBLICATIONS

Gormley et al, Chem Abstr vol. 118 entry 102309e (1992).

Gilbert et al. Chem Abstr vol. 117 entry 82802j (1992).

Steroids, 14, 269–283(1969), by Nayfeh, et al., "*Metabolism of Progesterone by Rat Testicular Homogenates-III*".

J. Pharm. Sc., 62, No. 4, pp. 638–640 (1973) by Doorenbos & Solomons, "*Synthesis & Antimicrobial Properties of 17 Beta-Isopentyloxy-4-Aza-5 Alpha-Androstane and the 4-Methyl Derivative*".

J. Pharm. Sci., 60, No. 8, pp. 1234–1235 (1971) by Doorenbos & Brown, "*4,17 Alpha-Dimethyl-4-Aza-5 Alpha-Androstan-17 beta-ol Acetate & Related Azasteroids*".

J. Pharm., 63, No. 4, pp. 620–622 (1974) by Doorenbos & Kim, "*Synthesis & Evaluation of Antimicrobial Properties of Amidinoazaandrostanes and Guanidinoazaandrostanes*".

J. Med. Chem. (1986) 29 (11): pp. 2298–3015 by Rasmusson, et al., "*Aza Steriods: Structure–Activity Relationship. . .*".

Prostate (1986) 9 (1): pp. 65–75 by Brooks, et al., "*Prostatic Effects Induced in Dogs By . . . 5 alpha–Reductase Inhibitors*".

Steroids (1986) 47 (1): pp. 1–19 by Brooks, et al., "*5 Alpha–Reductase Inhibitory . . . Activities of Some 4-Aza-Steriods in the rat*".

Endocr. (1985) 117 (2): pp. 571–579, by Liang, et al., "*Species Differences in Prostatic Steriodal 5 Alpha-Reductases of Rat, Dog and Human*".

J. Med. Chem. (1984) 27 (12: pp. 1690–1701, by Rasmusson, et al., "*Azasteroids as Inhibitors of Rat Prostatic 5 alpha-reductase*".

J. Org. Chem. (1981) Vol. 46, No. 7, pp. 1442–1446, T. Back, et al.

Chem. Abstracts, Vol. 95, 109055j, by T. Liang, et al. "Inhibition of 5 Alpha-Receptor Binding . . . by a 4-Methyl-4-Aza-Steroid" (1981).

JNCI, vol. 74, No. 2, pp. 475–481 (Feb. 1985), by N. Kadohama, et al., "*Retardation of Prostate Tumor Progression in the Noble Rat by 4-Methyl-4-Aza-Steroidal Inhibitors of 5 Alpha-Reductase*".

The Prostate vol. 10. pp. 189–197 (1987) by G. Andriole, et al., "*The Effect of 4MA . . . on the Growth of . . . Human Tumours . . .*".

J. Endocr., vol. 57, pp. 111–121 (1973) by K. D. Bingham, et al., "*the Metabolism of Testosterone by Human Male Scalp Skin*".

Bioorganic Chemistry, 17, pp. 372–376 (1986) by B. W. Metcalf, et al., "*Patent Inhibition of Human Steroid . . . by 3-Androstene-3-Carboxylic Acid*".

Biochemistry, 1990, vol. 29, pp. 2815–2824, by M. A. Levy, et al., "*Inhibition of Rat Liver Steroid 5 Alpha-Reductase . . .*".

J. Med. Chem. 1990, vol. 33, pp. 943–950, by D. A. Holt, et al. "*Steroidal A Ring Carboxylic Acids . . .*".

J. Steroid Biochem., vol. 34, Nos. 1–6, pp. 571–575 (1989), by M. A. Levy, et al., "*Interaction Between Rat Prostatic 5 Alpha-Reductase . . .*".

J. Med. Chem., vol. 33, pp. 937–942 (1990) by D. A. Holt, et al., "*Steroidal A Ring Aryl Carboxylic Acids*".

TIPS, Dec. 1989, vol. 10, pp. 491, 493–495, by D. W. Metcalf, et al., "*Inhibitors of . . . 5 Alpha-Reductase in Benign Prostatic Hyperplasia . . .*". *page 492 is missing.*

Steroids, vol. 35, No. 3 (Mar. 1980) pp. 1–7, by L. Murphy, et al., "*Effect of Estradiol on a . . . Binding Protein in the Uterus of the Mouse*".

Prostate, vol. 9, pp. 311–318 (1986) by N. Stone, et al., "*Estrogen Formation in Human Prostatic Tissue . . .*".

Lancet, No. 1986, No. 8515, pp. 1095–1096, by F. Labrie, et al., "*Combination therapy in prostate cancer*".

J. Clin. Endocrin. and Metab., vol. 55, No. 1, pp. 188–193 (1987), by R. Rittmaster, et al., "*The Effects of . . . a 5 Alpha-Reductase Inhibitor . . .*".

J. Clin. Endocrin and Metab., vol. 74, No. 2, pp. 345–350 (1990), by A. Diani, et al., "*Hair Growth Effects of Oral Adminstration of Finasteride . . .*".

J. Clin. Endocrinol. Metab. 67, No. 4, pp. 808–816 (1988), by N. Bruchovsky, et al., "*Kinetic Parameters of 5 Alpha-Reductase Activity in Stroma & Epithelium of Normal, Hyperplastic, & Carcinomatous Human Prostates*".

(List continued on next page.)

OTHER PUBLICATIONS

J. Steroid Biochem. 26, (3) pp. 349-353 (1987), by R. Hudson, "*Comparison of Nuclear 5 Alpha-Reductase Activities in the Stromal and Epithelial Fractions of Human Prostatic Tissue*".

J. Biol. Chem. 251, (19) pp. 5895-5900 (1976), by R. J. Moore, et al., "*Steroid 5 Alpha-Reductase in Cultured Human Fibroblasts*".

J. Biol. Chem. 264, (27) pp. 16249-16255 (1989), by S. Andersson, et al., "*Expression Cloning & Regulation of steroid 5 alpha-Reductase, an Exzyme Essential for Male Sexual Differentiation*".

Proc. Nat'l Acad. Science 87, pp. 3640-3644 (1990), by S. Andersson, et al., "*Structural & Biochemical Properties of cloned and expressed human and rat steroid 5 alpha-reductases*".

Nature 354, pp. 159-161 (Nov. 14, 1991), by S. Andersson, et al., "*Deletion of Steroid 5 Alpha-Reductase-2 Gene in Male Pseudohermaphroditism*".

Biol. of Reproduction, vol. 46, pp. 168-173 (1992), by J. D. Wilson, "*Syndromes of Androgen Resistance*".

Eur. J. Cancer 26(2), p. 188 (1990), by A. A. Geldof, et al., "*Enzyme Inhibitors in Hormone Dependent Prostate Cancer Growth*".

J. Cancer Res. Clin. Oncol. 118, pp. 50-55 (1992), by A. Geldof, et al. "*Consideration of the Use of . . . 4MA . . . in Prostate Cancer Therapy*".

The Prostate 18, pp. 215-227 (1991), by J. Brooks, et al., "*Effect of Castration, DES, Flutamide, and MK-906 on Growth of the Dunning Rat Prostatic Carcinoma . . .* ".

Eur. J. Pharm. 183(5), p. 1757 (1990), by Y. Masubuchi, et al., "*Lack of DHT Inhibition . . . by Treatment of 4MA . . .* ".

15-SUBSTITUTED 4-AZASTEROIDS

FIELD OF THE INVENTION

The present invention provides novel compounds, novel compositions, methods of their use and methods of their manufacture, where such compounds are generally pharmacologically useful as agents in therapies whose mechanism of action rely on the selective inhibition of the isozyme 5α-reductase 1.

BACKGROUND OF THE INVENTION

Certain undesirable physiological manifestations, such as acne vulgaris, seborrhea, female hirsutism, male pattern baldness (alopecia) and benign prostatic hyperplasia, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neff, et al., Endocrinol., Vol. 91, No. 2 (1972). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone, formed locally in the target organ by the action of testosterone-5α-reductase. Inhibitors of testosterone-5α-reductase will serve to prevent or lessen symptoms of hyperandrogenic stimulation. It is now known that a second 5α-reductase isozyme exists, which interacts with epidermal tissues, especially in scalp tissues. This form is conventionally designated as 5α-reductase 1, while the isozyme that principally interacts with the prostatic tissues is designated as 5α-reductase 2. Both isozymes are active in the prostatic tissues. Thus, in the treatment of hyperandrogenic disease conditions, e.g. benign prostatic hyperplasia (BPH), it would be desirable to have one drug entity which is active against both isozymes in the prostate to significantly inhibit dihydrotestosterone production, while also having another drug entity which is highly selective for inhibiting the isozyme 5α-reductase 1 associated with the scalp, for use in treating conditions of the skin and scalp, e.g. acne and alopecia in males and hirsutism in females. Additionally, such a selective 5α-reductase 1 inhibitor could also be used in combination with finasteride (PROSCAR ®), which is highly selective for 5α-reductase 2, for combination therapy in the treatment of BPH.

SUMMARY OF THE INVENTION

The compounds of the present invention are those of the general structural formula:

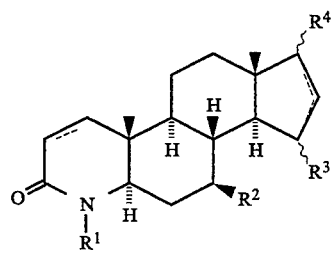

or a pharmaceutically acceptable salt or ester thereof, wherein $R^1$ is selected from the group consisting of hydrogen and $C_{1-10}$ alkyl;

$R^2$ is selected from the group consisting of hydrogen and $C_{1-10}$ alkyl;

$R^3$ is selected from the group consisting of $C_{1-10}$ alkyl, $C_{2-10}$ alkenyl, $C_{1-10}$ alkoxyl, cyano, hydroxyl and triphenylthio-$C_{1-6}$ alkyl;

$R^4$ is either monosubstituted by a substituent selected from the group consisting of keto, spiro-dioxolane and oximino or is disubstituted by hydrogen and $R^5$;

$R^5$ is selected from the group consisting of hydrogen, hydroxyl, Alk-$R^6$, Alk-X-Alk-$R^6$, Het and unsubstituted or substituted phenyl where said substituent is halogen, $C_{1-6}$ alkyl or $C_{1-6}$ alkoxyl;

$R^6$ is selected from the group consisting of hydrogen, hydroxyl, —CO—$R^7$, COO—$R^7$, —CO—NH—$R^7$, —NH—CO—$R^7$ and phenyl;

$R^7$ is selected from the group consisting of hydrogen, $C_{1-6}$ alkyl, pyridyl and unsubstituted or substituted phenyl where said substituent is halogen, $C_{1-5}$ alkoxyl, $C_{1-5}$ alkylcarbonyl, $C_{1-5}$ alkoxycarbonyl, or $C_{1-5}$ alkylaminocarbonyl;

X is O or NH;

Alk is $C_{0-10}$ alkyl (i.e. when C=0, there is no Alk moiety) or $C_{2-10}$ alkenyl; and Het is selected from the group consisting of pyridyl, thiophene, morpholinyl and thiazole.

More preferred are compounds of the general formula

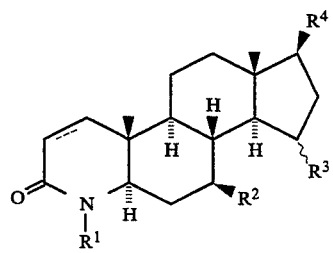

or a pharmaceutically acceptable salt or ester thereof, wherein $R^1$ is selected from the group consisting of hydrogen and $C_{1-10}$ alkyl;

$R^2$ is selected from the group consisting of hydrogen and $C_{1-10}$ alkyl;

$R^3$ is selected from the group consisting of $C_{1-10}$ alkoxyl, $C_{1-10}$ alkyl and cyano;

$R^4$ is selected from the group consisting of $C_{1-10}$ alkenyloxyl, $C_{1-10}$ alkoxyl, $C_{1-10}$ alkyl, $C_{1-10}$ alkylcarbamic, $C_{1-10}$ alkylcarbonyloxyl, carbonyl, hydroxyl, and —NH$R^5$; and $R^5$ is selected from the group consisting of hydrogen and $C_{1-10}$ alkylcarbonyl.

Most particularly preferred compounds are those of the following group:

4, 15β-dimethyl-17β-propyloxy-4-aza-5α-androstan-3-one;
15β-ethyl-17β-hydroxy-4-aza-5α-androstan-3-one;
4-methyl-15β-methoxy-17β-hydroxy-4-aza-5α-androstan-3-one;
4-methyl-15β-cyano-17β-hydroxy-4-aza-5α-androstan-3-one;
15β-ethyl-17-keto-4-aza-5α-androstane-3-one;
4-methyl-15β-methoxy-17β-allyloxy-4-aza-5α-androstan-3-one;
4, 15β-dimethyl-17β-amino-4-aza-5α-androstan-3-one;
4, 15β-dimethyl-21-isopentyl-4-aza-5α-pregnan-3-one;
4, 15β-dimethyl-17β-(2,2-dimethyl-propanoylamino)-4-aza-5α-androstan-3-one;
4, 15β-dimethyl-17β-(4-methyl-n-pentanoylamino4-aza-5α-androstane;
4-methyl-15β-methoxy-17β-n-propyloxy-4-aza-5α-androstan- 3 -one;
4, 15β-dimethyl-17β-hydroxy-4-aza-5α-androstan-3-one;
4, 15β-dimethyl-17β-(tert-butyl-aminocarbonyloxy)-4-aza-5α-androstan-3-one;
4-methyl-15β-ethyl-4-aza-5α-androstan-3, 17-dione;
4, 15β, 17β-trimethyl-4-aza-5α-androstan-3-one;
4, 15β-dimethyl-4-aza-5α-androstan-3, 17-dione;
4-methyl-15β-ethyl-17β-hydroxy-4-aza-5α-androstan-3-one;
4-methyl-15α-isopropyl-4-aza-5α-androstan-3, 17-dione;
4-methyl-15β-isopropyl-4-aza-5α-androstan-3, 17-dione;
4-aza-15β-ethyl-17α-n-propyloxy-5α-androstan-3-one,
4-aza-15β-methyl-17α-hydroxy-5α-androst-1-en-3-one;
4, 15β-dimethyl-4-aza-5α-androstan-3-one;
4-aza-15β-methyl-17β-hydroxy-5α-androstan-3-one;
4-methyl-15β-methoxy-4-aza-5α-androstan-3, 17-dione;
4, 15β-dimethyl-17β-(2, 2-dimethylpropanoyloxy)-4-aza-5α-androstan-3-one;
4-aza-15β-methyl-5α-androstan-3, 17-dione;
4-methyl-15β-cyano-4-aza-5α-androstane-3, 17-dione;
4, 7β, 15-trimethyl-17β-hydroxy-4-aza-5α-androstan-3-one;
4, 7β, 15-trimethyl-17β-allyloxy-4-aza-5α-androstan-3-one;
4, 7β, 15-trimethyl-4-aza-5α-androstan-3, 17-dione;
4-aza-15β-methyl-17β-hydroxy-5α-androstan-3-one; and
4-aza-15β-ethyl-5α-androstan 3, 17-dione.

DETAILED DESCRIPTION OF THE INVENTION

These compounds are useful for inhibiting the 5α-reductase isozymes 1 and 2, and are particularly useful in selectively inhibiting the 5α-reductase isozymes I associated with the scalp, and additionally inhibiting both isozymes 1 and 2 in the treatment of benign prostatic hyperplasia, acne, female hirsutism, male pattern baldness, androgenic alopecia, and prostatitis.

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/disphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "alkenyl" shall mean straight or branched chain alkenes with one or more degrees of unsaturation at any position on the chain, of two to ten total carbon atoms, or any number within this range.

Whenever the terms "alkyl" or "alkenyl" or either of their prefix roots appear in a name of a substituent (e.g. aralkoxyaryloxy) they shall be interpreted as including those limitations given above for "alkyl" and "alkenyl". Designated numbers of carbon atoms (e.g. $C_{1-10}$) shall refer independently to the number of carbon atoms in an alkyl or alkenyl moiety or to the alkyl or alkenyl portion of a larger substituent in which alkyl or alkenyl appears as its prefix root.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as an antiandrogenic agent.

The dosage regimen utilizing the compounds of the present invention is selected m accordance with a variety of factors including: type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 1000 mg/day orally. The compositions are preferably provided in the form of scored tablets containing 0.5, 1.0, 2.5, 5.0, 10.0, 15.0, 25.0 and 50.0 mg of active ingredient. Effective plasma levels of the compounds of the present invention range from 0.002 mg to 50 mg per kg of body weight per day. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen. Other preferred topical preparations include creams, ointments, lotions, aerosol sprays and gels, wherein the concentration of active ingredient would range from 0.1% to 15%, w/w or w/v.

In the methods of the present invention, the compounds herein described in detail can form the active ingredient, and are typically administered in admixture with suitable pharmaceutical diluents, excipients or carders (collectively referred to herein as "carder" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carder such as ethanol, glycerol, water, and the like. Moreover, when desired or necessary. suitable binders, lubricants, disintegrating agents and coloring agents can also be incorporated into the mixture. Suitable binders include starch, gelatin, natural sugars such as glucose or beta-lactose, com sweeteners, natural and synthetic gums such as acacia, tragacanth or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carders. Such polymers can include polyvinylpyrrolidone, pyran copolymer, polyhydroxypropyl-methacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Scheme 1

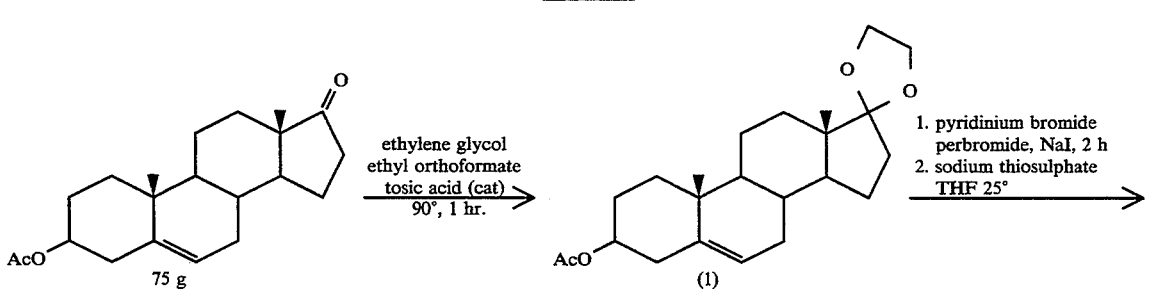

-continued
Scheme 1
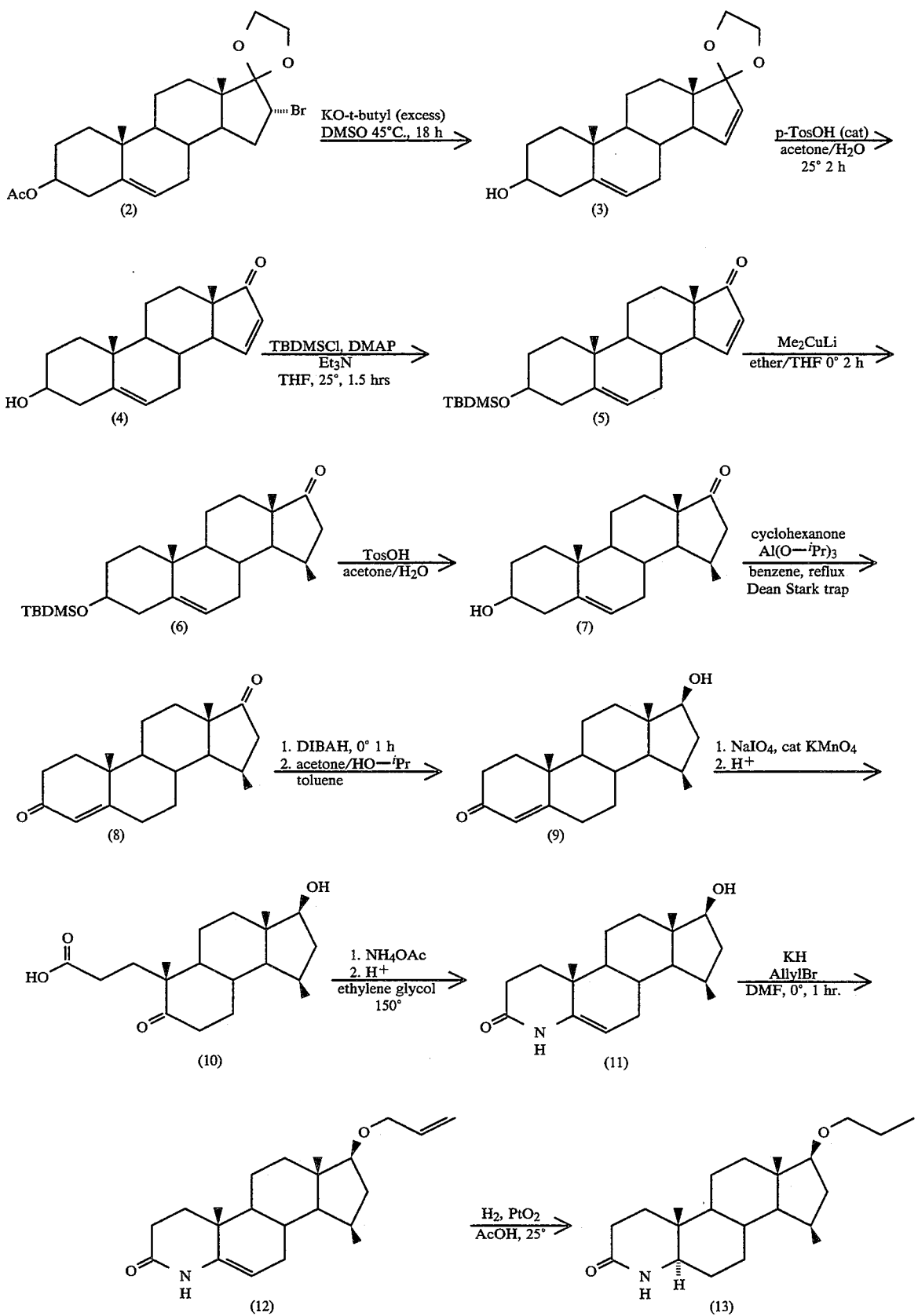

Scheme 2
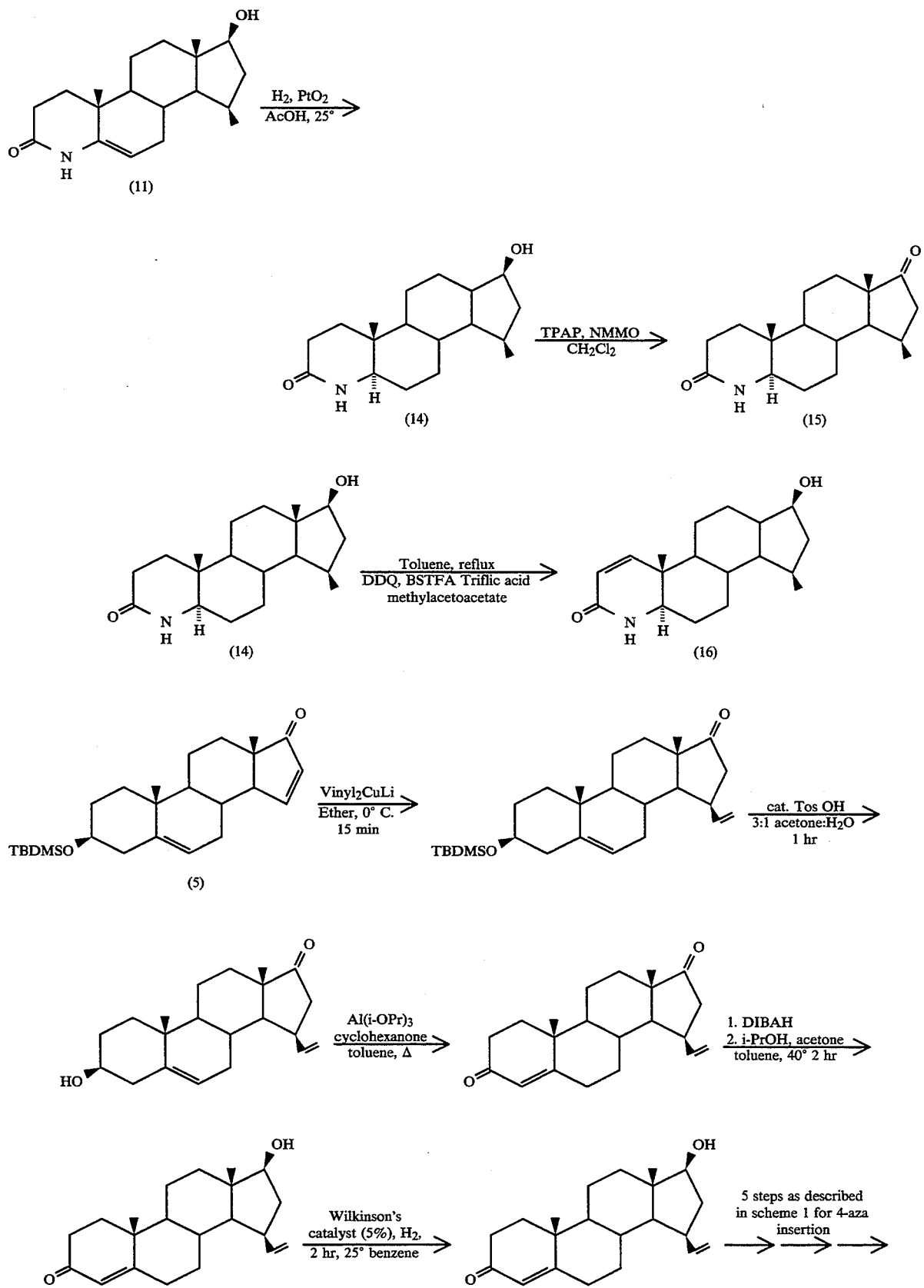

-continued
Scheme 2
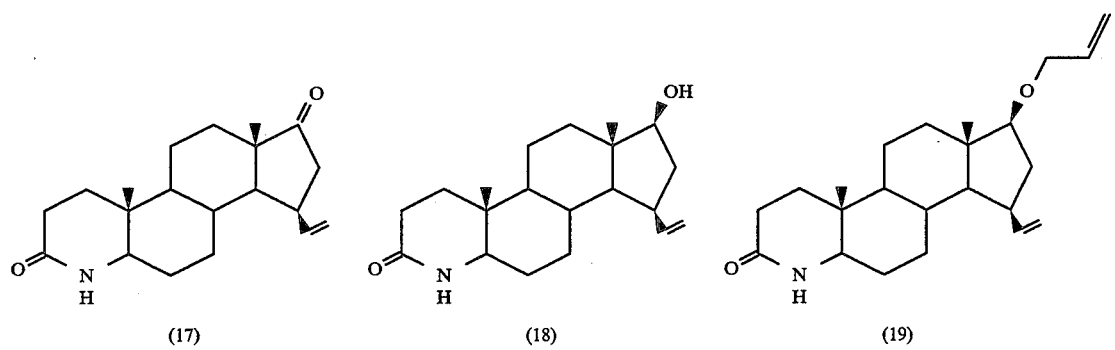
Scheme 3
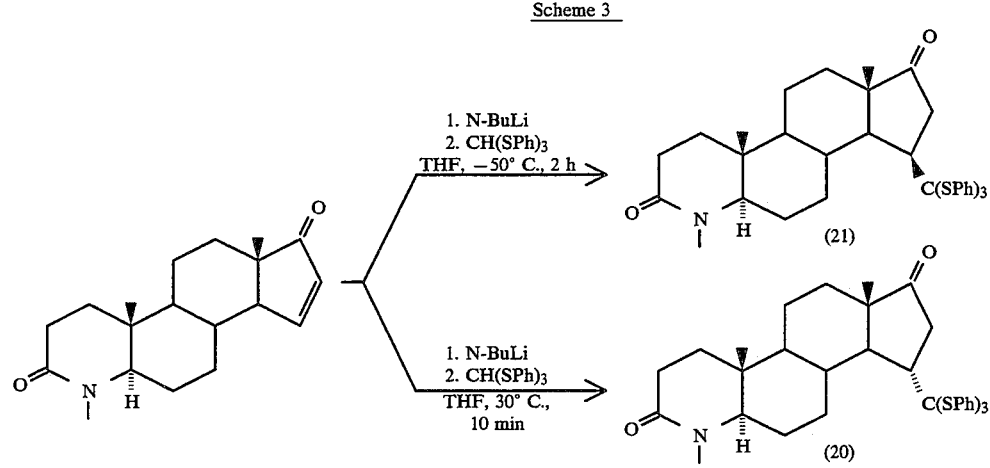
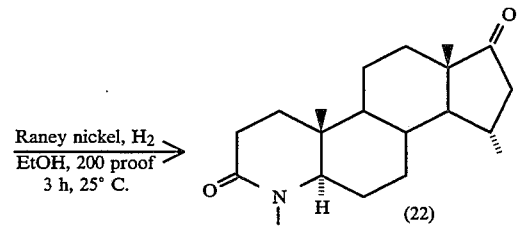
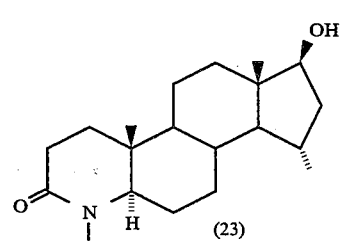
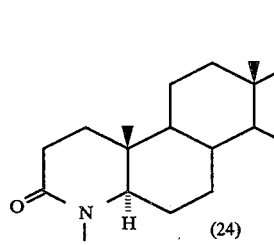
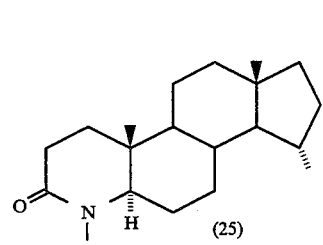
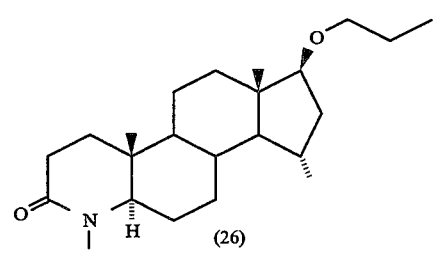
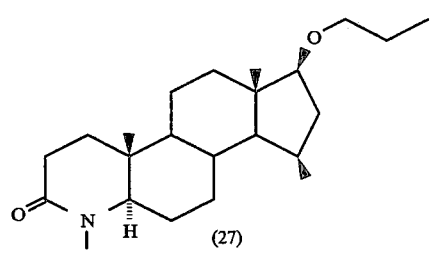

5,359,071

Scheme 4

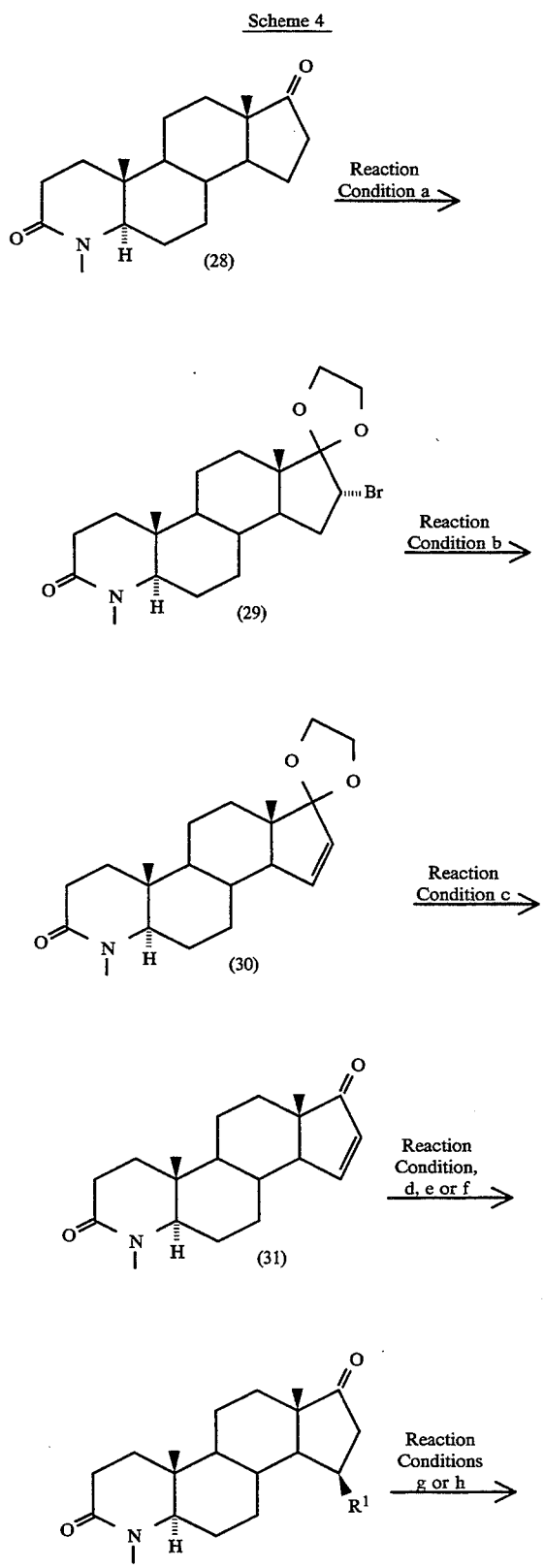

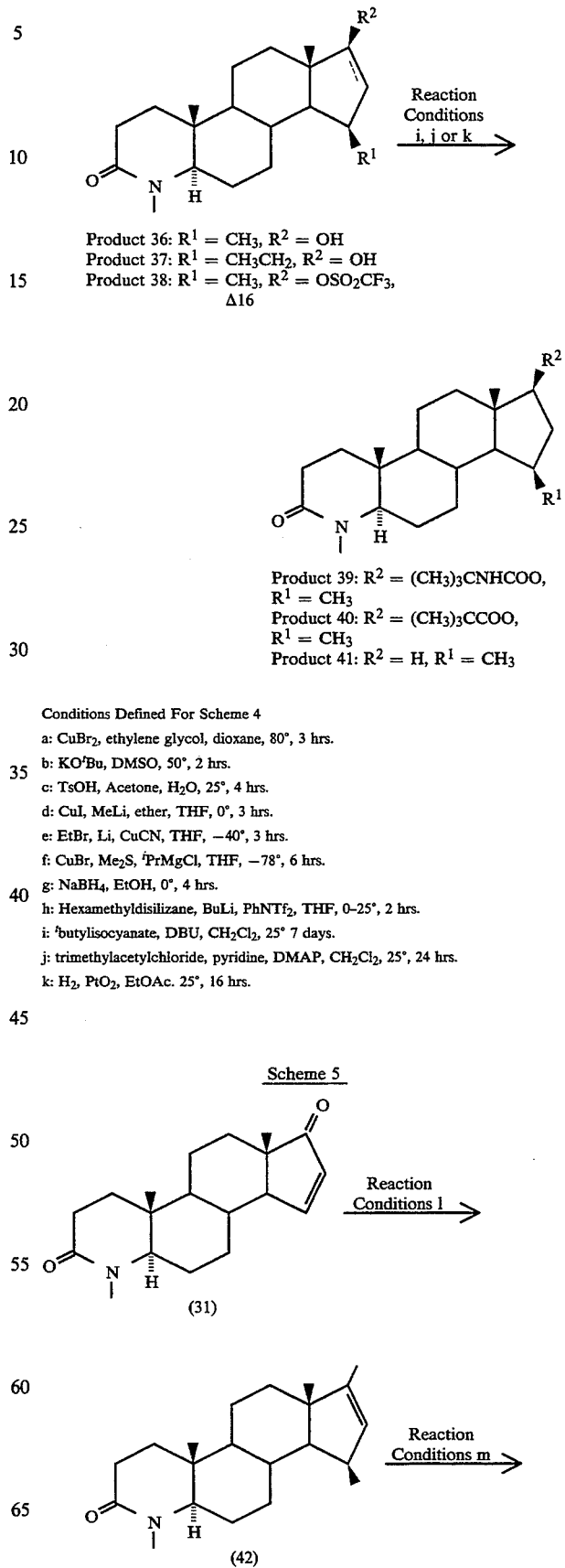

Product 36: $R^1 = CH_3$, $R^2 = OH$
Product 37: $R^1 = CH_3CH_2$, $R^2 = OH$
Product 38: $R^1 = CH_3$, $R^2 = OSO_2CF_3$, $\Delta 16$ Product 39: $R^2 = (CH_3)_3CNHCOO$, $R^1 = CH_3$
Product 40: $R^2 = (CH_3)_3CCOO$, $R^1 = CH_3$
Product 41: $R^2 = H$, $R^1 = CH_3$ Product 32: $R^1 = \beta\text{-}CH_3$
Product 33: $R^1 = \beta\text{-}CH_3CH_2$
Product 34, 35: $R^1 = \alpha\text{-}, \beta\text{-}(CH_3)_2CH$ Conditions Defined For Scheme 4
a: CuBr₂, ethylene glycol, dioxane, 80°, 3 hrs.
b: KO^tBu, DMSO, 50°, 2 hrs.
c: TsOH, Acetone, H₂O, 25°, 4 hrs.
d: CuI, MeLi, ether, THF, 0°, 3 hrs.
e: EtBr, Li, CuCN, THF, −40°, 3 hrs.
f: CuBr, Me₂S, ^iPrMgCl, THF, −78°, 6 hrs.
g: NaBH₄, EtOH, 0°, 4 hrs.
h: Hexamethyldisilizane, BuLi, PhNTf₂, THF, 0–25°, 2 hrs.
i: ^tbutylisocyanate, DBU, CH₂Cl₂, 25° 7 days.
j: trimethylacetylchloride, pyridine, DMAP, CH₂Cl₂, 25°, 24 hrs.
k: H₂, PtO₂, EtOAc. 25°, 16 hrs.

Scheme 5

Scheme 5
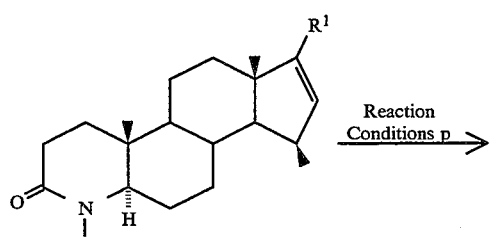
(43)
Scheme 6
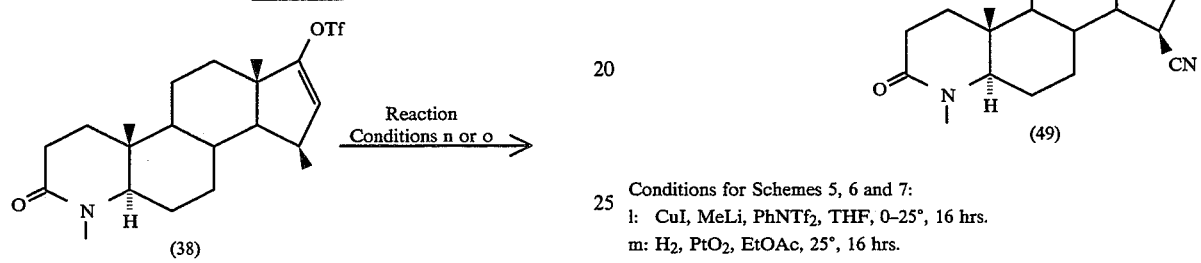
(38)
Product 44: R¹ = (CH₃)₂CH(CH₂)₂CC
Product 45: R¹ = CH₃O₂CCHCH
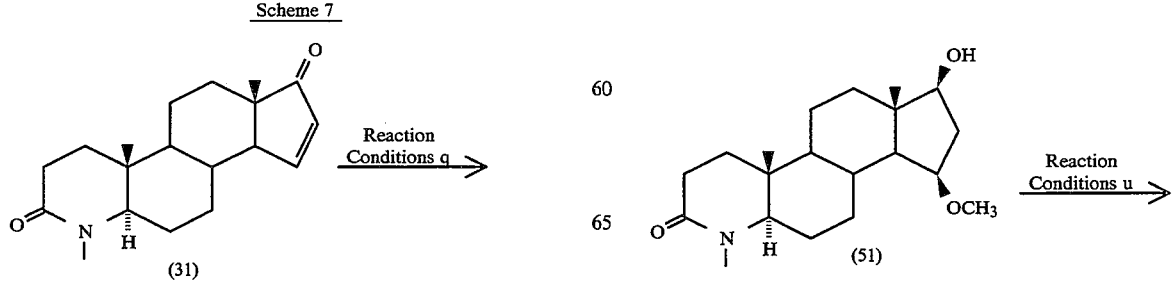
Product 46: R¹ = (CH₃)₂CH(CH₂)₄
Product 47: R¹ = CH₃O₂CCH₂CH₂
Scheme 7
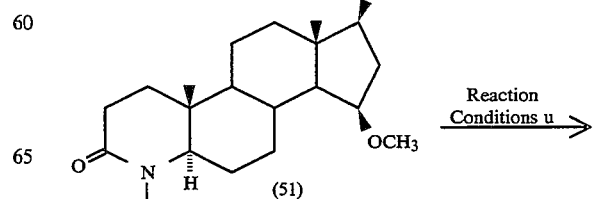
(31)
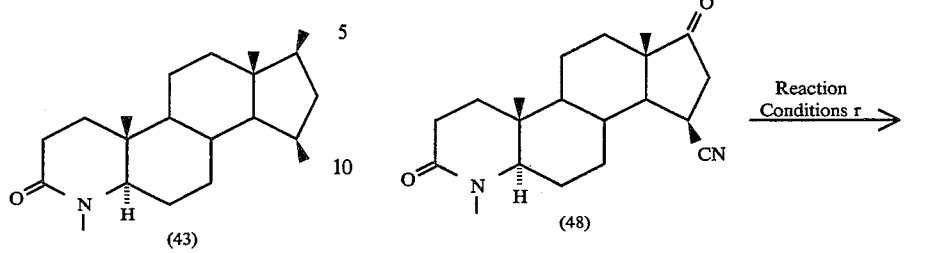
(48)
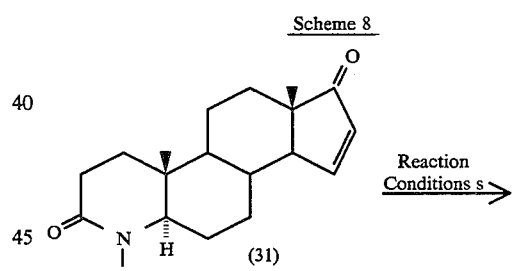
(49)
Conditions for Schemes 5, 6 and 7:
l: CuI, MeLi, PhNTf₂, THF, 0–25°, 16 hrs.
m: H₂, PtO₂, EtOAc, 25°, 16 hrs.
n: 5-methyl-1-hexyne, (Ph₃P)₂Pd(OAc)₂, CuI, (ⁱPr)₂NH, DMF, 25°, 16 hrs.
o: methyl acrylate, (Ph₃P)₂Pd(OAc)₂KOAc, DMF, 60°, 12 h.
p: H₂, PtO₂, EtOAc, MeOH, 25°, 16 hrs.
q: KCN, THF, 60°, 3 hrs.
r: NaBH₄, EtOH, 0°, 4 hrs.
Scheme 8
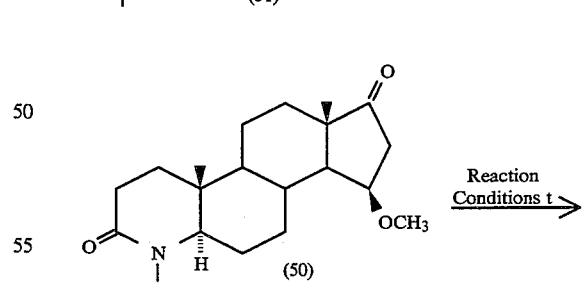
(31)
(50)
(51)

17
-continued
Scheme 8

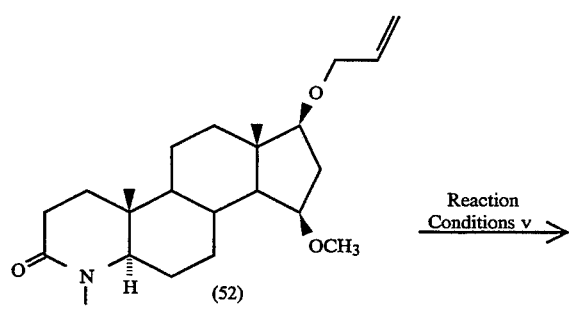

18
-continued
Scheme 9

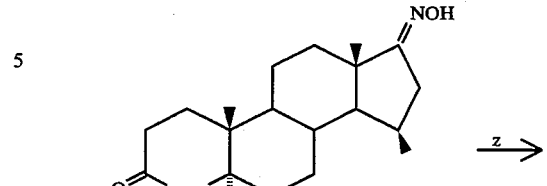

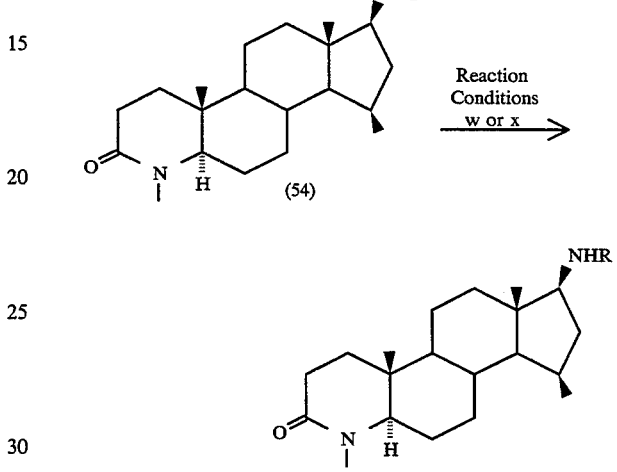

55: R = COC(CH₃)₃
56: R = COCH₂CH₂CH(CH₃)₂

Reaction Conditions for Schemes 8 and 9:
s: NaOMe, MeOH, 25°, 1 hr.
t: NaBH₄, EtOH, 0°, 4 hrs.
u: KH, Allylbromide, DMF, 0°, 1 hr.
v: H₂, 10% Pd on Carbon, MeOH, 25°
w: Trimethylacetyl chloride, pyridine, CH₂Cl₂, 25°, 6 hrs.
x: 4-methylvaleric acid, 1-hydroxybenzotriazole hydrate, 1-(3-Dimethylamino-propyl)-3-ethylcarbodiimide hydrochloride, THF, 25°, 16 hrs.
y: NH₂OH.HCl, NaOAc, EtOH, 80°, 6 hrs.
z: H₂, PtO₂, EtOH, 25°

Scheme 9

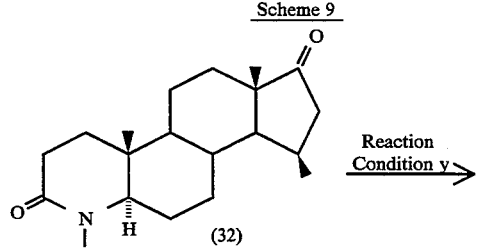

Scheme 10

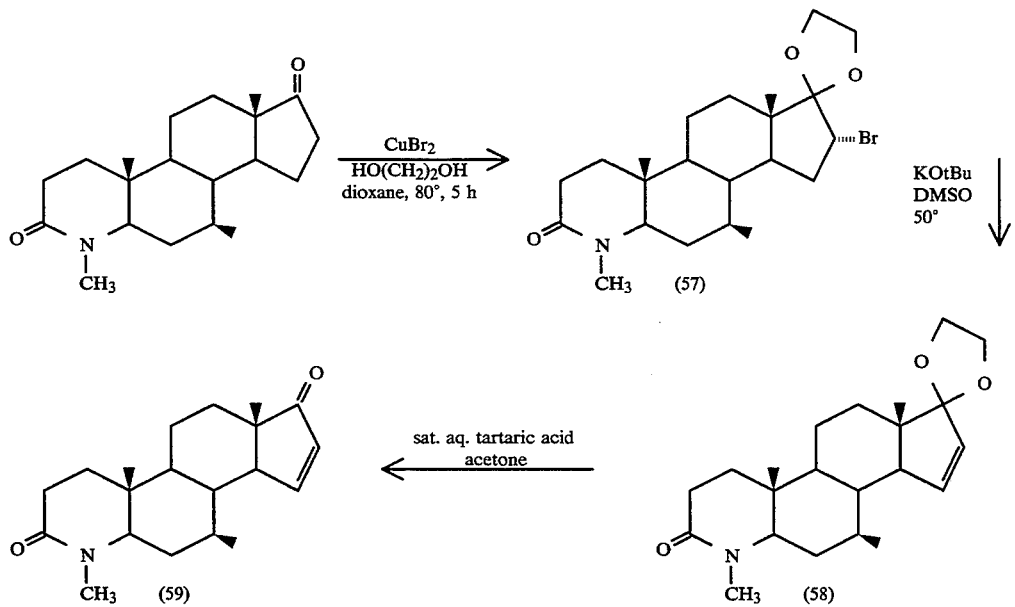

-continued
Scheme 10

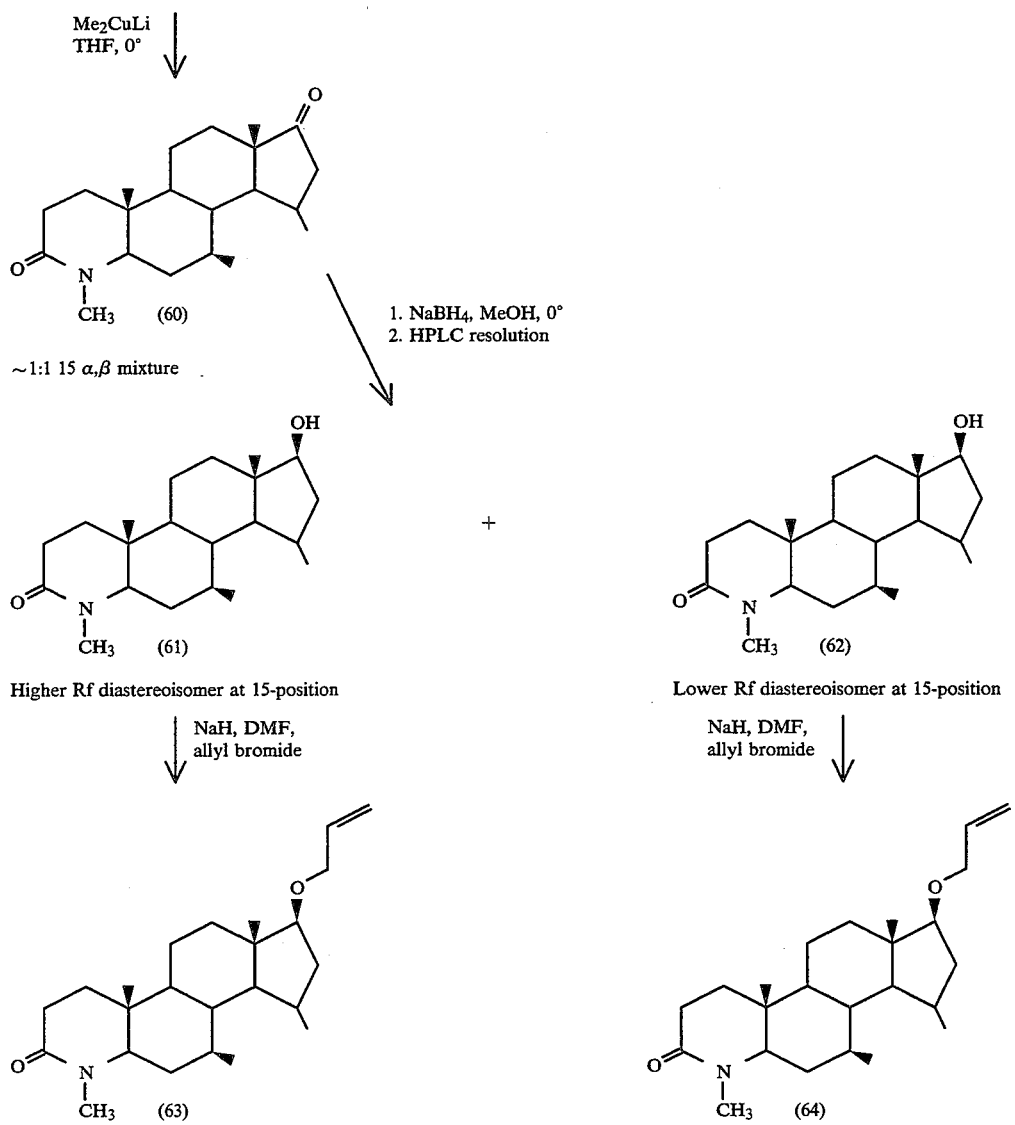

EXAMPLE 1

3β-Acetoxy-17-ethylenedioxyandrost-5-ene (1)

Toluene-p-sulphonic acid (1.0 g, 5.2 mmole), 3β-acetoxyandrost-5-ene-17-one (didehydroepiandrosterone acetate) obtained as described in D. Liu et. al., *J. Chem, Soc.. Perkin Trans. I,* p 2161 (1988), the entire disclosure of which is incorporated herein by reference, (50 g, 151.4 mmol), ethylene glycol 18.6 mL, 520 mmol), and triethylorthoformate (72 mL, 428 mmole) were stirred together at 90° and refluxed under anhydrous conditions. After 1 h, the solvent was slowly distilled off and the distillation was continued until the temperature of the mixture reached 110° C. The hot mixture was poured cautiously into hot methanol (285 mL) containing pyridine (8 mL). Water (72 mL) was then added and the solution allowed to cool slowly to room temperature. The crystals were filtered off and dried to give the title acetal (52.3 g, 92%), mp=143° δH (CDCl$_3$) 0.86 (s, 3H), 1.03 (s, 3H), 2.03 (s, 3H), 3.75–4.05 (m, 4H, 17-acetal), 4.48–4.73 (m, 1H), and 5,38 (brd, 1H, J 4.5 Hz).

EXAMPLE 2

3β-Acetoxy-16α-bromo-17-ethylenedioxyandrost-5-ene (2)

The acetal (1) (40 g, 107 mmol) was dissolved in freshly distilled anhydrous THF (120 ml). Pyridinium bromide perbromide (80 g, 250 mmol) in 120 mL THF was added and the resulting mixture stirred for 2 h. Sodium iodide (60 g, 403 mmol) was added and stirring continued for 30 min. A solution of sodium thiosulphate (80 g) in 120 mL of water and pyridine (24 mL) was added and the resulting solution stirred for 3 h. The mixture was diluted with water (250 mL) and the THF evaporated off under reduced pressure. The crystalline material was filtered off, washed well with water, dried and recrystallized from aqueous ethanol to give the 16α-bromo derivative (45 g, 99 mmol, 93%) δ$_H$(CDCl$_3$) 0.90 (s, 3H), 1.02 (s, 3H), 2.03 (s, 3H), 3.85–4.05 (m, 2H), 4.10–4.20 (m, 1H), 4.20–4.30 (m, 1H), 4.50–4.70 (m, 1H), 4.50–4.60 (dd, J$_1$=10.5, J$_2$=4.5 Hz), and 5.36 (br d, 1H).

EXAMPLE 3

3β-Hydroxy-17-ethylenedioxy androst-5,15-diene (3)

Product (2) (17 g, 37.5 mmol) was dissolved in dry dimethyl sulphoxide (DMSO, 170 mL) at 40°–45°. Dry potassium t-butoxide (13.5 g, 120 mmol) was added under nitrogen and the mixture left at 40°–45° C. overnight (18 h). The solution was then poured into dry ether (1000 mL) and stirred for 10 minutes to dissolve any solids. Water was added 15 (500 mL) and the ethereal solution was washed with water followed by saturated brine. The solution was dried (MgSO$_4$), filtered and evaporated to dryness. Recrystallization of the residue from aqueous ethanol gave the diene $\delta_H$ (CDCl$_3$) 0.94 (s, 3H), 3.46–3.63 (m, 1H), 3.79–4.08 (m, 4H), 5.37 (br d, 1H), 5.71 (dd, J=3.3 Hz, 1H), and 6.13 (br d, J=4.8 Hz, 1H).

EXAMPLE 4

3.β-Hydroxy-androstan-5,15-diene-17-one (4)

The diene (3) (5.9 g, 16.8 mmole) was dissolved in 150 mL of acetone. and 15mL of H$_2$O. p-Toluene sulphonic acid (250mg, 1.3 mmol) was added and the solution stirred at 4°. overnight. Water was added (75 mL) and the solvent removed under reduced pressure at 25°. A precipitate formed and was filtered, washed with cold water and dried under vacuum. The 17-ketone was recovered:(4.4 g, 96%), mp=186–188° $\delta_H$(CDCl$_3$) 1.09 (s, 3H), 1.59 (s, 3H), 3.50–3.60 (m, 1H), 5.41 (m, 1h), 6.05 (dd, J=3 and 6Hz, 1H) and 7.51 (br d, J=6 Hz, 1H).

EXAMPLE 5

3β-(Dimethyl-butylsilyloxy)-androstan-5.15-diene-17-one (5)

To the dienone (4), (4.4 g, 15.3 mmol) in dichloromethane (40 mL) was added t-butyldimethylsilyl chloride (5.61 g, 37 mmol), dry triethylamine (5.6 mL, 40 mmol) and 4-dimethylaminopyridine (4.52 g, 37 mmol). The mixture was stirred at 200 for 5 h, then water was added along with additional methylene chloride (200 mL and 50 mL, respectively). The mixture was extracted with methylene chloride, pooled, washed sequentially with 10% aqueous ammonium chloride, saturated brine, dried over MgSO$_4$, filtered and the solvent removed under reduced pressure. The residue was chromatographed with 70/30 dichloromethane/hexane on a flash silica gel column. Recovered 4.4 g (11 mmole, 72%) of product $\delta_H$(CDCl$_3$) 1.05 (s, 3H), 1.06 (s, 3H), 3.20–3.60 (m, 1H), 5.38 (d, 3 Hz, 1H), 6.03 (dd, J=3 and 6 Hz, 1H), and 7.47 (br d, J=6 Hz, 1H).

EXAMPLE 6

3β-(Dimethyl-t-butylsilyloxy)-15β2 -methyl-androst-5-EN-17-one (6)

A 250 mL round bottomed flask fitted with a stirrer bar and rubber septum was flamed dried under nitrogen. Copper (I) iodide (6.21 g, 32.8 mmol) was added and the flask flushed with N$_2$. A 2:1 mixture (v/v) of dried diethyl ether (120 mL) and tetrahydrofuran (60 mL) was cannulated into the flask and the solution cooled to 0°. Two equivalents of methyl lithium (1.6 N, 41 mL, 66 mmol) was slowly added to the reaction mixture while insuring that the solution temperature remained below 5°. The solution was stirred until all of the copper iodide was consumed (30 min). The enone (5) (3.30 g, 8.2 mmol) was added via syringe in 40 mL of dry THF over 5 min, again keeping the solution temperature below 5°. The mixture was stirred at 0° for 1 h, then 10 ml of 10% ammonium choride was carefully added dropwise over 10 min. This mixture was stirred 15 minutes, then 100 mL of dichloromethane was added, the mixture extracted and the organic phase was decanted. The aqueous phase was extracted with 3×50 ml dichloromethane. The organic layer was pooled, dried over MgSO$_4$, filtered and the volume reduced under reduced pressure. The product was chromatographed (75/25 dichloromethane/hexane). Product recovered: (3.10 g, 7.5 mmol, 70%) $\delta_H$ (CDCl$_3$) 1.01 (s, 3H), 1.03 (s, 3H), 1.09 (d, J=7 Hz,), 3.4–3.5 (m, 1H), 5.34 (d, 1H).

EXAMPLE 7

3β-Hydroxy-5-ene-15β-methyl-androst-5-ene-17-one (7)

A 100 mL round bottomed flask was fitted with a stir bar and filled with 60 mL of a 5:1 solution of acetone: water and 3.1 g of 6. The solution was warmed to 50° and p-toluenesulfonic acid (800 mg, 4.2 mmol) was added. This was stirred until the silyl protecting group was removed (2 h). The solution volume was reduced under reduced pressure and 100 mL of water was added. The product precipitated out of solution and was isolated by filtration on a fritted glass funnel and washed with 3×30 mL of ice water. The product was dried overnight under reduced pressure. Recovered product: (2.28 g, 7.5 mmol, 95%) $\delta_H$ (CDCl$_3$) 1.01 (s, 3H), 1.04 (s, 3H), 1.09 (d, J=7 Hz, ), 3.45–3.55 (m, 1H), 4.82 (bs, 1H), 5.39 (d, 1H).

EXAMPLE 8

15β-methyl-androst-4-ene 3,17-DIone (8)

A 50 mL round bottomed flask is fitted with a stir bar, 26 mL of dry benzene, 2.28 g of (2.1 and 7 mL of cyclohexanone. The flask is fitted with a Dean Stark trap attached to a condenser. The solution is refluxed and 3 mL of solvent is removed (water azeotrope). Then 10 mL more of toluene with 1.44 g (7.1 mmol) of aluminum isopropoxide is added to the flask and 10 mL of distillate is removed by reflux over 2 h. Cool to 65° and add 600mg each of Darco activated charcoal and Celite filter aid with 1 mL of water. Stir for 1 h and filter through a sintered glass funnel and wash the precipitate with 6×15 mL of hot ethyl acetate. Reduce the filtrate volume under reduced pressure and chromatograph the product by flash chromatography with a 4/1 mixture of hexane/ethyl acetate. Recovered product (1.5 g, 5 mmol, 63%) $\delta_H$(CDCl$_3$) 1.05 (s, 3H), 1.13 (d, J=7 Hz,), 1.22 (s, 3H), 5.73 (d, 1H).

EXAMPLE 9

15β-Methyl-17-β-hydroxy-androst-4-ene 3-one (9)

A 250 mL round bottomed flask was fitted with a stirrer bar and was flame dried under nitrogen. Then enone (8) (1.5 g, 5 mmol) and 75 mL of toluene was added and the flask sealed with a rubber septum. The solution was cooled to −78° and diisobutylaluminum hydride (7.5 mL, 25% solution in toluene) was added dropwise, keeping the temperature under −60°. This was stirred for 1 h at −78°. 3 mL of acetone was slowly added dropwise, then 3 mL of isopropanol, keeping the temperature under −30°. The solution was slowly warmed up to room temperature and stirred for 1 h. Another 1 mL of acetone was added and the solution was warmed to 35° for 2 h. By TLC, we saw a single, slightly lower strongly UV active spot, indicating that the 3-enone has been reformed. Workup was performed by pouring the solution into 5% sodium hydrogen sulphate. The solution was then acidified with 2 N $H_2SO_4$ to pH=3, extracted with 1:1 ether: ethyl acetate and chromatographed on silica gel with 3:2 hexane: ethyl acetate. Recovered product: (1.33 g, 89%) $\delta_H$ (CDCl$_3$) 0.89 (s, 3H), 1.00 (d, J=7 Hz,), 1.18 (s, 3H), 3.58 (m, 1H), 5.70 (d, 1H).

EXAMPLE 10

15$\beta$-Methyl-androstan-17$\beta$-ol seco acid (10)

Periodate cleavage of (9) was effected by dissolving sodium periodate (6.52 g, 30.5 mmol), potassium permanganate (48 mg, 0.3 mmole) and sodium carbonate (680 mg, 6.4 mmole in 25 mL of hot water) and adding this solution dropwise over 20 minutes to a refluxing solution of 9 (1.33 g, 4.4 mmol) in 30 mL of tert-butanol. The suspension was refluxed for 1 h after the addition is complete, cooled to 30° and filtered with washing (3×10 mL of hot $H_2O$). The filtrate was concentrated under reduced pressure to remove the tert-butanol and then acidified to pH=3 with 5 N hydrochloric acid. The product was extracted with 4×20 mL of dichloromethane, the extracts pooled and dried over MgSO$_4$. The solvent was removed under reduced pressure. Recovered product: 1.24 g (3.7 mmol, 84%). The product was used without further purification $\delta_H$ (CDCl$_3$) 0.92 (s, 3H), 1.02 (d, J=7 Hz), 1.13 (s, 3H), 3.58 (m, 1H).

EXAMPLE 11

15$\beta$-Methyl-17$\beta$-hydroxy-4-aza androst-5-en-3-one (11)

The secoacid (10) (1.24 g, 3.7 mmol) was mixed with ammonium acetate (1.7 g, 22.2 mmol) and ethylene glycol (23 mL) in a 50 mL round bottomed flask fitted with a stirrer bar and a rubber septum. The flask was heated under nitrogen to 1800 slowly over 40 minutes at kept there for 2 h. The mixture was cooled to 70° and the solution poured into 200 mL of ice water. The product precipitated out, was filtered and washed with water. The precipitate was dried under reduced pressure. Recovered product: (0.72 g, 2.2 mmol, 61%) $\delta_H$ (CDCl$_3$) 0.90 (s, 3H), 0.99 (d, J=7 Hz,), 1.11 (s, 3H), 3.60 (t, J=7 Hz, 1H), 4.81 (m, 1H), 7.37(bs, 1H).

EXAMPLE 12

15$\beta$-Methyl-17$\beta$-allyloxy-4-aza-androst-5-EN-3-one (12)

Potassium hydride (40% oil dispersion, 114 mg, 2 mmol) was added to a 5 mL round bottomed flask fitted with a stirrer bar and a rubber septum. The potassium hydride dispersion was washed with dry hexane (2×5 ml) to remove the mineral oil and 3 mL of dry dimethylformamide was added to the flask. Azasteroid (11) (158 mg, 0.5 mmol) was added to the dispersion and the solution stirred at 0° under nitrogen for 1 h. Then allyl bromide (183 mg, 1.5 mmol) was syringed into the solution and the mixture stirred for 2 h at room temperature. The entire solution was poured into 5 mL of 1N HCl and the mixture extracted with 5×2 mL of dichloromethane. The pooled organic layer was washed with 3×5 mL of saturated brine. The product was flash chromatographed with 3/1 dichloromethane/ethyl acetate. Recovered product (78 mg, 0.2 mmol, 44%) $\delta_H$ (CDCl$_3$) 0.89 (s, 3H), 0.99 (d, J=7 Hz,), 1.06 (s, 3H), 3.60 (m, J=7 Hz, 1H), 3.95 (dd, J=12 Hz, J=5 Hz), 4.64 (dd, J=12 Hz, J=5 Hz), 5.1 ( m, 2H), 5.79 (m, 1H).

EXAMPLE 13

15$\beta$-Methyl-17$\beta$-propyloxy-4-aza-5$\alpha$-androstan-3-one (13)

Azasteroid (12) (78 mg, 0.2 mmol) was hydrogenated in 1 mL of ethanol with stirring over 20mg of platinum oxide under a hydrogen atmosphere. The reaction was complete after 2 h at 400. The solution was filtered to remove the platinum catalyst. The solution was added to 10 mL of water. The product crystallized out of solution and was dried under reduced pressure. Recovered product: 48 mg (61%). $\delta_H$ (CDCl$_3$) 0.85 (t, J=7 Hz, 3H), 0.87 (s, 3H), 0.89 (s, 3H), 0.99 (d, J=7 Hz,), 2.65 (m, 2H), 3.3 (m, 2H), 3.82 (t, J=7 Hz, 1H), 3.95 (m, 1H), Mass spectrum (M+ =347).

EXAMPLE 14

17$\beta$-Hydroxy-15$\beta$-methyl-4-aza-5$\alpha$-androstan-3-one (14)

Intermediate (11) (0.2 g, 0.65 mmole) was dissolved in 3 mL of glacial acetic acid. Platinum oxide (25 mg) was added, the flask sealed with a rubber septum and hydrogen gas was introduced via syringe with stirring at 25°. No starting material was seen by TLC after 2 h. The reaction mixture was filtered and the solvent removed under reduced pressure. The product was recrystallized from ethyl acetate. Recovered product: (0.15 g, 75%) H (CDCl$_3$) 0.87 (s, 3H), 0.92 (s, 3H), 0.98 (d, J=7 Hz, ), 2.40 (m, 2H), 3.08 (dd, =12 Hz, J=5 Hz), 3.58(t, J=9 Hz, 1H), 5.72 (bs, 1H) Mass spectrum (M+ =305).

EXAMPLE 15

15-Methyl-4-aza-5$\alpha$-androstan-3,17-dione (15)

Compound 14 (40 mg, 0.126 mmole) was dissolved in 3 mL of dichloromethane in a 10 mL round bottomed flask fitted with a stirrer bar and rubber septum. The solution was cooled to 0° and 100 mg of 4 angstrom powdered molecular sieve, 210 mg of N-methyl morpholine N-oxide (1.7 mmole) and tetrapropylammonium perruthenate (3 mg, 0.01 mmol) were added and stirred for 2 h. Analysis by TLC (95/5 dichloromethanne/methanol) indicated that starting material was gone. The product was purified by flash chromatography (97/3 dichloromethane/methanol). Recovered product: 35 mg, 0.110 mmole) $\delta_H$ (CDCl$_3$) 0.94 (s, 3H), 1.02 (s, 3H), 1.10 (d, J=7 Hz, ), 2.42 (m, 2H), 3.1 (dd, =12 Hz, J=4 Hz), 5.78 (bs, 1H) Mass spectrum (M+ =303).

EXAMPLE 16

17$\beta$-Hydroxy-15$\beta$-methyl-4-aza-5$\alpha$-androst-1-en-3-one (16)

Compound (14) (55 mg, 0.17 mmole), dichlorodicyano benzoquinone (DDQ) (47 mg, 0.21 mmole), bis(trimethylsilyl)trifluoroacetamide (BSTFA) (175 mg, 0.68 mmole) and trifluoromethanesulfonic acid (2 mg, 0.0013 mmol) were stirred overnight in 2 mL of toluene in a 5 mL round bottomed flask fitted with a stirrer bar and condenser. The next day 40 microliters of methyl acetoacetate was added to quench the red colored DDQ complex which was then refluxed overnight. The solution was then diluted with 5 mL dichloromethane and the solution extracted sequentially with 25 mL of water, 10 mL of water with 400 mg of sodium carbonate, and 150mg of sodium sulfite in 5 mL of water. The layers were separated and the organic phase washed with 5% sodium bicarbonate, dried over Mg SO$_4$, filtered and the solvent removed under reduced pressure. Purification was by flash chromatography (9/1 dichoromethane/acetone). Recovered product: (26 mg, 47%) $\delta_H$(CDCl$_3$) 0.92 (s, 3H), 0.99 (s, 3H), 1.01 (d, J=7 Hz,), 2.53 (m, 1H), 3.35 (dd, J=12 Hz, J=4 Hz), 5.5 (bs, 1H), 5.80 (d, J=10 Hz, 1H), 6.81 (d, J=10 Hz, 1H) Mass spectrum (M+ =303).

Refer to Schemes 1 and 2 for the procedural workup for Examples 17, 18 and 19.

EXAMPLE 17

17$\beta$-Ethyl-4-aza-5$\alpha$-androstane-3-17-dione (17)

$\delta_H$(CDCl$_3$) 0.89( t, J=7 Hz, 3H), 0.92 (s, 3H), 0.97 (s, 3H), 2.45 (m, 2H), 3.07 (dd, J=12 Hz, J=3Hz, 1H), 5.67 ( bs, 1H): Mass spectrum (M+ =317).

EXAMPLE 18

17$\beta$-Hydroxy-15$\beta$-ethyl-4-aza-5$\alpha$-androstan-3-one (18)

$\delta_H$ (CDCl$_3$) 0.81 (t, J=7 Hz), 0.83 (s, 3H), 0.89 (s, 3H), 2.32 (m, 1H), 2.43 (m, 1H), 3.08 (dd, J=12 Hz, J=4 Hz), 3.60 (t, J=7 Hz, 1H) Mass spectrum (M+ =319).

EXAMPLE 19

151$\beta$-Ethyl-17$\beta$-propyloxy-4-aza-5$\alpha$-androstan-3-one (19)

$\delta_H$(CDCl$_3$) 0.85 (t, J=7 Hz, 3H), 0.87 (s, 3H), 0.89 (s, 3H), 0.99 (d, J=7 Hz,), 2.65 (m, 2H), 3.3 (m, 2H), 3.82 (t, J=7 Hz, 1H), 3.95 (m, 1H), Mass spectrum (M+ =361).

EXAMPLE 20

4-Methyl-15$\alpha$-(tris(phenylthio)-methane)-4-aza-5$\alpha$-androstan-3,17-dione (20)

To a 50 mL round bottomed flask flamed under nitrogen, fitted with a stirrer bar and sealed with a rubber septum was added tris(phenylthio) methane (850 mg, 2.5 mmol) and 30 mL of dry tetrahydrofuran. The solution was cooled to −78° with a dry ice/acetone bath and 1.05 equivalents of 1.6 N n-butyllithium (1.56 mL, 2.1 mmole) is added slowly to the solution. The temperature was allowed to come to 25°. Then 31, as prepared in Scheme 4, (0.60 g, 2.0 mmole) in 5 mL of dry tetrahydrofuran was cannulated dropwise over 5 min into the reaction mixture. The solution was stirred for 1 h and then quenched with 2 mL of 30% ammonium chloride. The solution was poured into 50 mL of water and extracted with 3×25 mL of dichloromethane. The organic layer was pooled, dried over MgSO$_4$, filtered and the solvent removed under reduced pressure. By NMR (400 MHz), we saw a 9/1 ratio of 15$\alpha$/15$\beta$ methyl product. Purification by flash chromatography (80/20 hexane/isopropanol) gave the higher R$_f$15$\alpha$ derivative (823 mg, 74%) $\delta_H$(CDCl$_3$) 0.73 (s, 3H), 0.91 (s, 3H), 2.32 (m, 1H), 2.05 (t, J=8 Hz 1H), 2.2 (m, 1H), 2.45 (q, J=5 Hz), 2.55 (dd, J=20, J=10 Hz), 2.70 (dd, J=14, J=7 Hz), 2.97 (s, 3H), 3.17 (dd, J=16 Hz, J=5 Hz), 3.83 (bd, 2H), 7.23-7.40 (m, 13H), 7.53-7.55 (m, 2H).

EXAMPLE 21

4-Methyl-15$\beta$-(tris(phenylthio)methane)-4-aza-5$\alpha$-androstane-3,17-dione (21)

To a 10 mL round bottomed flask flamed under nitrogen, fitted with a stirrer bar and sealed with a robber septum was added tris(phenylthio) methane (134 mg, 0.4 mmol) and 3 mL of dry tetrahydrofuran. The solution was cooled to −78° with a dry ice/acetone bath and 1.05 equivalents of 1.6 N n-butyllithium (0.25 mL, 0.4 mmole) was added slowly to the solution. The temperature was allowed to come to −40°. Then 4-aza-methyl-androstan-15-ene-3,17-dione 31, (0.10 g, 0.33 mmole) in 1 mL of dry tetrahydrofuran was cannulated dropwise into the reaction mixture. The solution was stirred for 1 h at −40° and then quenched with 1 mL of 30% ammonium chloride. The solution was poured into 5 mL of water and extracted with 3×5 mL of dichloromethane. The organic layer was pooled, dried over MgSO$_4$, filtered and the solvent removed under reduced pressure. By NMR (400 MHz), we saw a 18/1 ratio of 15$\beta$/15$\alpha$ methyl product. Purification by flash chromatography (80/20 hexane/isopropanol) gave the lower R$_f$15$\beta$ derivative (175 mg, 90%) $\delta_H$(CDCl$_3$) 0.90 (s, 3H), 1.55 (s, 3H), 2.43(m, 2H), 2.88 (s, 3H), 3.21 (dd, J=16 Hz, J=5 Hz), 7.23-7.40 (m, 13H), 7.53-7.55 (m, 2H).

EXAMPLE 22

4,15$\alpha$-Dimethyl-4-aza-5$\alpha$-androstan-3,17-dione (22)

4-aza-methyl-15$\alpha$-(tris(phenylthio)methane)-androstane-3,17-dione (18) (650 mg, 1.12 mmol) was dissolved in 25 mL of absolute ethanol. Then 4 g of W2 Raney Nickel (Aldrich) was thoroughly washed with absolute ethanol (10×10 mL), added to the reaction mixture and the product agitated under hydrogen (STP) for 18 h at 25°. The reaction mixture was filtered and the Raney Nickel washed with ethanol to give about 150 mL of filtrate. The solvent was removed under reduced pressure and the solid chromatographed on silica gel (80/20 dichloromethane/acetone) to give the desired product 22 (300 mg, 84%): $\delta_H$(CDCl$_3$) 0.89 (s, 3H), 0.91 (s, 3H), 1.15 (d, J=6 Hz), 1.70 (dd J=20 Hz, J=8 Hz), 2.43 (m, 2H), 2.70 (dd J=20 Hz, J=8 Hz), 2.90 (s, 3H), 3.03 (dd, J=12 Hz, J=3 Hz) Mass spectrum (M+ =317).

EXAMPLE 23

4,15$\alpha$-Dimethyl-17$\beta$-hydroxy-4-aza-5$\alpha$-androstan-3-one (23)

$\delta_H$(CDCl$_3$) 0.65 (t, J=9 Hz, 1H), 0.76 (s, 3H), 0.88 (s, 3H), 1.02 (d, J-6 Hz), 2.40 (q, J=5 Hz, 2H), 2.90 (s, 3H), 2.98 (dd, J=12 Hz, J=3 Hz), 3.65 (bt, 1H): Mass spectrum (M+ =319).

EXAMPLE 24

4,15$\alpha$-Dimethyl-17$\beta$-allyloxy-4-aza-5$\alpha$-androstan-3-one (24)

$\delta_H$(CDCl$_3$) 0.65 (t, J=9 Hz, 1H), 0.80 (s, 3H), 0.87 (s, 3H), 1.00 (d, J=7 Hz), 2.40 (q, J=5 Hz, 2H), 2.90 (s, 3H), 2.98 (dd, J=12 Hz, J=3 Hz), 3.35 (t, J=8 Hz, 1H), 3.97 (d, J=7 Hz, 2H), 5.12 (dd, J=12 Hz, J=3 Hz, 1H), 5.25 (dd, J=18 Hz, J=3 Hz, 1H), 5.8-5.9 (m, 1H): Mass spectrum (M+ =359).

EXAMPLE 25

4,15$\alpha$-Dimethyl-4-aza-5$\alpha$-androstan-3-one (25)

$\delta_H$(CDCl$_3$) 0.57 (t, J=10 Hz, 1H), 0.72 (s, 3H), 0.86 (s, 3H), 1.02 (d, J=7 Hz), 2.40 (q, J=5 Hz, 2H), 2.89 (s, 3H), 2.98 (dd, J=12 Hz, J=3 Hz): Mass spectrum (M+ =303).

EXAMPLE 26

4,15α-Dimethyl-17β-propyloxy-4-aza-5α-androstan-3-one (26)

$\delta_H$(CDCl$_3$) 0.65 (t, J=9 Hz, 1H), 0.78 (s, 3H), 0.87 (s, 3H), 1.01(d, J=Hz), 2.40 (q, J=5 Hz, 2H), 2.90 (s, 3H), 2.98 (dd, J=12 Hz, J=3 Hz), 3.35 (m, 2H), 4.3 (m, 1H): Mass spectrum (M+=361).

EXAMPLE 27

4,15β-Dimethyl-17β-propyloxy-4-aza-5α-androstan-3-one (27)

$\delta_H$(CDCl$_3$) 0.889 (s, 3H), 0.893 (s, 3H), 0.98(d, J=7 Hz), 2.43 (q, J=5 Hz, 2H), 2.91 (s, 3H), 3.25 (m 1H), 3.35 (m, 2H): Mass spectrum (M+=361).

EXAMPLE 28

4-Methyl-4-aza-5α-androstan-3,17-dione (28)

$\delta_H$ (CDCl$_3$) 0.85(s, 3H), 0.89 (s, 3H), 2.92 (s, 3H) 3.85–4.0 (m, 2H), 4.05–4.15 (m, 1H), 4.20–4.25 (m, 1H), 4.50–4.60 (dd, J$_1$=10.5, J$_2$=4.5 Hz).

EXAMPLE 29

4-Methyl-16α-bromo-17-(3-dioxolane)-4-aza-5α-androstan-3-one (29).

$\delta_H$(CDCl$_3$) (0.85 (s, 3H), 0.86 (s, 3H), 2.89 (s, 3H).

EXAMPLE 30

4-Methyl-17-(1,3-dioxolane)-4-aza-5α-androstan-15-EN-3-one (30)

(See also *J. Chem. Soc. Perkin Trans.* 1 1988, 2161, the entire disclosure of which is incorporated herein by reference) 16.76 g (39.3 mmol) of (29), 9.26 g (82.5 mmol) of potassium tert-butoxide and 200 mL of DMSO were combined together and stirred at 50° in a flask fitted with a condenser for 2 hours. The mixture was diluted with CH$_2$Cl$_2$ and sat. NaCl, and the aqueous layer extracted with CH$_2$Cl$_2$. The organic layer was washed with sat. NaCl, dried over MgSO$_4$, filtered and concentrated in vacuo. The product was crystallized from CH$_2$Cl$_2$ with ethyl ether to obtain 9.18 g of whim solid. The mother liquor was purified by MPLC on a 40×350 mm silica column by eluding with 15% acetone/CH$_2$Cl$_2$. 2.29 g of a white solid was recovered from the column. Yield=84%.

EXAMPLE 31

4-Methyl-4-aza-5α-androst-1.5 ene-3,17 dione (3.1)

(See also *J. Chem. Soc. Perkin Trans.* 1 1988, 2161, the entire disclosure of which is incorporated herein by reference). To a solution of 11.07 g (32.0 mmol) of (30) in 500 ml of acetone at 25° was added 1.22 g (6.4 mmol) of p-toluenesulfonic acid monohydrate followed by 50 ml H$_2$O. This mixture was stirred at 25° for 4 hours, then the acetone was evaporated in vacuo. The resulting solution was diluted with sat. NaHCO$_3$ and CH$_2$Cl$_2$, and the aqueous layer extracted with CH$_2$Cl$_2$. The organic layer was dried over K$_2$CO$_3$, filtered, and concentrated in vacuo. Crystallization of this solid from CH$_2$Cl$_2$ with ethyl ether yielded the product contaminated with a lower R$_f$ impurity, so it was dissolved in CH$_2$Cl$_2$ and repurified by MPLC on a 40×700 mm silica column by eluting with 8.0 L of 15% acetone/CH$_2$Cl$_2$. 8.63 g of a white solid was recovered from the column. Yield=89%.

EXAMPLE 32

4,15β-Dimethyl-4-aza-5α-androstan-3,17-dione (32)

(See also *J. Chem. Soc. Perkin Trans.* 1 1998, 1994, the entire disclosure of which is incorporated herein by reference). To a solution of 628 mg (3.3 mmol) of copper(I) iodide in 5 ml THF at 0° under N$_2$ was added 4.7 ml (6.6 mmol) of methyllithium (1.4 M in ether) dropwise with stirring. This solution was stirred for 15 min., then a solution of 200 mg (0.66 mmol) of (31 ) in 2 ml THF was added dropwise. Stirring was continued at 0° for 2 hours, then at 25° overnight. The reaction mixture was poured into sat. NH$_4$Cl with stirring, then diluted with EtOAc, and the organic layer separated. The aqueous layer was extracted with CH$_2$Cl$_2$, then the organic layers were combined and washed with sat. NH$_4$Cl and sat. NaCl, dried over MgSO$_4$, filtered, and concentrated in vacuo. The resulting solid was purified by MPLC on a 21×300 mm silica column by eluding with 1.0 L of 15% acetone/CH$_2$Cl$_2$. 150 mg of white solid was recovered from the column. Yield=72%.

EXAMPLE 33

4-Methyl-15β-ETHYL-4-aza-5α-androstan-3,17-dione (33)

(See also *Tet. Lett.* 1982, 23(37), 3755 and *J. Med. Chem.* 1971, 14(3), 194, the entire disclosure of which is incorporated herein by reference). 220 mg (7.91 mmol) of lithium dispersion (25% in mineral oil) was washed with hexane and kept under N$_2$ atmosphere. To this was added 10 ml of THF and the slurry was cooled to −20°. To this was added 295 µl (3.95 mmol) of ethylbromide dropwise with stirring. In a separate flask, 177 mg (1.98 mmol) of copper(I) cyanide was azeotropically dried with toluene, then kept under N$_2$. 2 ml of THF was added to the CuCN and this slurry was cooled to −40°. To this was added the ethyllithium solution at −40° via canula and the reaction was stirred for 3 hours. To this was added a solution of 100 mg (0.33 mmol) (31 ) in 3 ml THF at −40° and stirring continued for 3 hours. The reaction was quenched with slow addition of sat. NH$_4$Cl, then diluted with EtOAc, and the organic layer separated. The aqueous layer was extracted with CH$_2$Cl$_2$. The organic layers were combined and washed with sat. NH$_4$Cl, H$_2$O, and sat. NaCl, dried over MgSO$_4$, filtered and concentrated in vacuo. The resultant oil was purified by MPLC on a 21×300 mm silica column by eluting with 1.0 L of 15% acetone/CH$_2$Cl$_2$. 27 mg of white solid was recovered from the column. Yield=25%.

EXAMPLES 34 AND 35

4-Methyl-15(α and β)-isopropyl-4-aza-5α-androstane-3,17-dione (34 and 35)

(See also *J. Org. Chem.* 1990, 55(12), 3954, the entire disclosure of which is incorporated herein by reference). To a solution of 135 mg (0.66 mmol) copper(I) bromide dimethylsulfide complex in 1 ml THF at −78° under N$_2$ was added 660 µl (1.32 mmol) isopropylmagnesium chloride (2.0 M in THF). This slurry was stirred for 30 min., then a solution of 100 mg (0.33 mmol) (31 ) in 1 ml THF was added to it, and stirring was continued at −78° for 6 hours. The reaction was quenched with 5 ml of sat. NH$_4$Cl, diluted with EtOAc, and the organic layer was separated. The aqueous layer was extracted with $CH_2Cl_2$. The organic layers were combined, dried over $MgSO_4$, filtered and concentrated in vacuo. The resulting oil was purified by MPLC on a 21×300 mm silica column by eluting 1.0 L of 15% acetone/$CH_2Cl_2$. 30 mg of a sticky white solid was recovered from the column. NMR and mass spec. of this material indicated it was a mixture of isomers at $C_{15}$. This material was further purified by HPLC with two passes through a 7.8×300 mm Waters Porosil column eluting with 15% isopropanol/hexane at 2.9 ml/min., but injecting with $CH_2Cl_2$. About 10 mg of each isomer was recovered from the column. Yield=18%.

EXAMPLE 36

4,Methyl-15$\beta$-Methyl-17$\beta$-hydroxy-4-aza-5$\alpha$-androstan-3-one (36)

To a stirred solution of 150 mg (0.47 mmol) of (32) in 2 ml ethanol at 0° is added 36 mg (0.94 mmol) sodium borohydride. Stirring was continued at 0° for 4 hours, then the reaction mixture was poured into 100 ml $H_2O$ and stirred. A precipitate formed and was collected by filtration, washed with $H_2O$, and dried under high vacuum. 89 mg of white solid was recovered. Yield=59%.

EXAMPLE 37

4-Methyl-15$\beta$-ethyl-17$\beta$-hydroxy-4-aza-5$\alpha$-androstane-3-one (37)

To a stirred solution of 24 mg (0.07 mmol) of (33) in 1 ml ethanol at 0° is added 6 mg (0.14 mmol) sodium borohydride. Stirring was continued at 0° for 6 hours, then the reaction mixture was poured into 1 ml $H_2O$ and stirred. The ethanol was evaporated in vacuo, then the aqueous layer was extracted with $CH_2Cl_2$. The organic layers were combined, dried over $MgSO_4$, filtered and concentrated under high vacuum. 15 mg of white solid was recovered. Yield=64%.

EXAMPLE 38

4,15$\beta$-Dimethyl-17-trifluoromethanesulfonyloxy-4-aza-5$\alpha$-androstan-16-ene-3-one (38)

(See also *Tet. Lett.* 1983, 24(10), 979, the entire disclosure of which is incorporated herein by reference.) 1.69 ml (8.03 mmol) hexamethyldisilizane was dissolved in 10 ml THF and cooled to 0°. Under a $N_2$ atmosphere, 2.78 ml (6.96 mmol) butyllithium (2.5 M in hexane) was added, followed by another 30 ml THF to dilute the precipitate that formed. This slurry was stirred for 15 min., then a solution of 1.70 g (5.35 mmol) (32) in 10 ml THF was added to it. This was stirred for 30 min. at 0°, then 2.87 g (8.03 mmol) N-phenyltrifluoromethanesulfonimide was added in one portion. The cooling bath was removed and the mixture was stirred. After 2 hours the reaction was diluted with EtOAc and sat. $NH_4Cl$. The aqueous layer was extracted with EtOAc. The organic layers were combined and washed with sat. $NaHCO_3$, $H_2O$, and sat. NaCl, dried over $Na_2SO_4$, filtered and concentrated in vacuo. The resulting oil was purified by MPLC on a 40×350 mm silica column by eluting with 10% acetone/$CH_2Cl_2$. 1.54 g of white solid was recovered from the column. Yield=64%.

EXAMPLE 39

4,15 $\beta$-Dimethyl-17$\beta$-tert-butyl-aminocarbonyloxy-4-aza-5$\alpha$-androstane (39)

40 mg (0.13 mmol) of (36), 1 ml $CH_2Cl_2$, 57 $\mu$l (0.50 mmol) tertbutylisocyanate, and 75 $\mu$l (0.50 mmol) 1,8-diazabicyclo[5.4.0]undec-7-ene (DBU) were combined and stirred at 25° for 7 days. The crude reaction mixture was then directly applied to a 21×300 mm silica column and purified by MPLC by eluding with 15% acetone/$CH_2Cl_2$. NMR and mass spec. of a white solid recovered from column indicated desired product.

EXAMPLE 40

4,15$\beta$-Dimethyl-17$\beta$-(tertbutylcarbonyloxy)-4-aza-5$\alpha$-androstan-3-one (40)

40 mg (0.13 mmol) of (36), 1 ml $CH_2Cl_2$, 62 $\mu$l (0.50 mmol) trimethylacetylchloride, 40 $\mu$l (0.50 mmol) pyridine, and a few crystals of N,N-dimethylaminopyridine were combined and stirred at 25° for 1 day. The crude reaction mixture was then directly applied to a 21×300 mm silica column and purified by MPLC by eluting with 1.0 L of 5% acetone/$CH_2Cl_2$, then 0.5 L of 15% acetone/$CH_2Cl_2$. NMR and mass spec. of white solid recovered from column indicated desired product.

EXAMPLE 41

4,15$\beta$-Dimethyl-4-aza-5$\alpha$-androstan-3-one (41)

45 mg of (38) was dissolved in 1 ml EtOAc. To this was added 5 mg platinum oxide and hydrogen gas by balloon reservoir. This mixture was stirred at 25° overnight, then the catalyst was removed by filtration and the solvent removed in vacuo. The resulting oil was purified by MPLC on a 21×300 mm silica column by eluting with 10% acetone/$CH_2Cl_2$. NMR and mass spec. of a white solid recovered from column indicated desired product.

EXAMPLE 42

4,15$\beta$,17-Trimethyl-4-aza-5$\alpha$-androst-16-ene-3-one (42)

(See also *J. Org. Chem.* 1990, 55(3), 964, the entire disclosure of which is incorporated herein by reference.) To a solution of 2.20 g (11.5 mmol) of copper(I) iodide in 15 ml THF at 0° under $N_2$ was added 16.5 ml (23.1 mmol) of methyllithium (1.4 M in ether) dropwise with stirring. This was stirred for 15 min., then a solution of 700 mg (2.31 mmol) of (31) in 6 ml THF was added dropwise. Stirring was continued at 0° for 2 hours, then at 25° overnight. The reaction was recooled to 0°, then a solution of 907 mg (2.54 mmol) N-phenyltrifluoromethanesulfonimide in 5 ml THF was added in one portion. The cooling bath was removed and the reaction stirred at 25° for 1 hour. The reaction was quenched by adding 50 ml sat. $NH_4Cl$ slowly, then diluted with EtOAc, and the organic layer separated. The aqueous layer was extracted with $CH_2Cl_2$. The organic layers were combined, washed with sat. $NH_4Cl$, $H_2O$, and sat. NaCl, dried over $MgSO_4$, filtered and concentrated in vacuo. The resulting oil was purified by MPLC on a 40×350 mm silica column by eluding with 3.5 L of 15% acetone/$CH_2Cl_2$. 510 mg of a white solid was recovered from column. Yield=70%.

EXAMPLE 43

4,15$\beta$17$\beta$-Trimethyl-4-aza-5$\alpha$-androstan-3-one (43)

50 mg of (42) was dissolved in I ml EtOAc. To this was added 5 mg platinum oxide and hydrogen gas by balloon. The mixture was stirred at 25° overnight, then the catalyst was removed by filtration and the solvent evaporated in vacuo. The resulting oil was purified by MPLC on a 21×300 mm silica column by eluting 10% acetone/CH$_2$Cl$_2$. NMR and mass spec. of white solid recovered from column indicated desired product.

EXAMPLE 44

4,15β-Dimethyl-20-yne-21-isopentyl-4-aza-5α-pregn-16-ene-3-one (44)

(See also *Synlett.* 1991, 409, the entire disclosure of which is incorporated by reference) 110 mg (0.24 mmol) of (38), 1 ml disopropylamine, 2 mg copper(I) iodide, 10 mg bis(triphenylphosphine)palladium(II) acetate, 39 μl (0.29 mmol) 5-methyl-1-hexyne, and 2 ml DMF were s combined at 25° in a flame-dried flask and stirred at 25° for 16 hours under nitrogen. The reaction was diluted with EtOAc and filtered to remove catalyst. The filtrate was washed with sat. NaHCO$_3$, H$_2$O, and sat. NaCl, dried over MgSO$_4$, filtered and concentrated in vacuo. The resulting oil was purified by MPLC on a 21×300 nun silica column by eluting 10% acetone/CH$_2$Cl$_2$. 69 mg of yellowish oil was recovered from column. Yield=73%.

EXAMPLE 45

4,15β-Dimethyl-16,20-Diene-21-(methoxycarbonyl)-4-aza-5α-pregnan-3-one (45)

(See also *Synthesis* 1986, 320, the entire disclosure of which is incorporated by reference) 750 mg (1.67 mmol) (38), 250 mg (0.33 mmol) bis(triphenylphosphine)palladium(II) acetate, 522 mg (6.67 mmol) potassium acetate, 601 μl (6.67 mmol) methyl acrylate, and 5 ml DMF were combined in a flask fitted with a condenser and stirred at 600 for 12 hours. The reaction was diluted with EtOAc and filtered to remove catalyst. The filtrate was washed with sat. NaHCO$_3$, H$_2$O, and sat. NaCl, dried over MgSO$_4$, filtered and concentrated in vacuo. The resulting oil was purified by MPLC on a 40×350 mm silica column by eluting 15% acetone/CH$_2$Cl$_2$. 665 mg of reddish solid was recovered from the column. NMR indicated product had a significant amount of degraded catalyst contaminating it, but it was used as is, and repurified again after reduction of the diene.

EXAMPLE 46

4,15β-Dimethyl-21-isopentyl-4-aza-5α-pregnan-3-one (46)

69 mg of (44) was dissolved in 2 ml EtOAc and 0.5 ml MeOH. To this was added 10 mg platinum oxide and hydrogen gas by balloon. The mixture was stirred at 25° overnight, then the catalyst was removed by filtration and the solvent evaporated in vacuo. NMR and mass spec. of the waxy solid recovered from filtration indicated desired product.

EXAMPLE 47

15β-Dimethyl-21-(methoxycarbonyl)-4-aza-5α-pregnan-3-one (47)

665 mg of (45) was dissolved in 10 ml EtOAc. To this was added 60 mg platinum oxide and hydrogen gas by balloon. The mixture was stirred at 25° overnight, then the catalyst was removed by filtration and the solvent evaporated in vacuo. The resulting oil was purified by MPLC on a 40×350 mm silica column by eluting 15% acetone/CH$_2$Cl$_2$. 360 mg of a whim solid was recovered from the column.

EXAMPLE 48

4-Methyl-15β-cyano-4-aza-5α-androstan-3,17-dione (48)

(See also *J. Org. Chem.* 1964, 29, 64, the entire disclosure of which is incorporated herein by reference.) To a solution of 125 mg (0.41 mmol) of (31) in 4 ml THF was added 268 mg potassium cyanide, followed by 3 drops of H$_2$O to help solubilize the KCN. This mixture was stirred at 25° for 2 hours, then at 60° for 3 hours. Then the reaction was diluted with EtOAc and H$_2$O, and the organic layer was separated. The aqueous layer was extracted with CH$_2$Cl$_2$, and the organic layers combined and concentrated in vacuo. The resulting oil was purified by MPLC on a 21×300 mm silica column by eluting with acetone/CH$_2$Cl$_2$. 20 mg of white solid was recovered from the column. Yield=15%.

EXAMPLE 49

4-Methyl-15β-CYANO-17β-hydroxy-4-aza-5α-androstan-3-one (49)

18 mg (0.05 mmol) of (48) was stirred in 1 ml EtOH at 0°, then 4 mg (0.11 mmol) sodium borohydride was added and this mixture was stirred at 0° for 4 hours, then diluted with H$_2$O and EtOH evaporated in vacuo. The aqueous layer was extracted with CH$_2$Cl$_2$. The organic layers were combined, dried over MgSO$_4$, filtered and concentrated in vacuo. The resulting oil was purified by MPLC on a 21×100 mm silica column by eluting a gradient from 20 to 50% with acetone/CH$_2$Cl$_2$. 10 mg of a white solid was recovered from the column. Yield=61%.

EXAMPLE 50

4-Methyl-15β-methoxy-4-aza-5α-androstane-3,17dione (50)

(See also *J. Org. Chem.* 1964, 29, 64, the entire disclosure of which is incorporated herein by reference.) 100 mg (0.33 mmol) of (31) was dissolved in 1 ml MeOH. To this was added 21 mg (0.40 mmol) sodium methoxide and the mixture was stirred at 25° for 1 hour. The reaction was dilute with sat. NaCl and CH$_2$Cl$_2$. The aqueous layer was extracted with CH$_2$Cl$_2$. The organic layers were combined, dried over MgSO$_4$, filtered and concentrated in vacuo. The resulting oil was purified by MPLC on a 21×300 mm silica column by eluting 15% with acetone/CH$_2$Cl$_2$. 65 mg of a white solid was recovered from the column. Yield=59%.

EXAMPLE 51

4-Methyl-15β-methoxy-17β-hydroxy-4-aza-5α-androstan-3-one (51)

60 mg (0.18 mmol) of (50) was stirred in 1 ml EtOH at 0°, then 14 mg (0.36 mmol) sodiumborohydride was added and this mixture stirred at 0° for 4 hours. The reaction was diluted with H$_2$O and the EtOH evaporated in vacuo. The aqueous layer was extracted with CH$_2$Cl$_2$. The organic layers were combined, dried over MgSO$_4$, filtered and concentrated in vacuo. The resulting oil was purified by MPLC on a 21×300 mm silica column by eluting with a gradient from 15 to 50% acetone/CH$_2$Cl$_2$. 35 mg of a white solid was recovered from the column. Yield=58%.

EXAMPLE 52

4-Methyl-15β-Methoxy-17β-allyloxy-4-aza-5α-androstan-3-one (52)

30 mg (0.09 mmol) of (51) was dissolved in 0.5 ml DMF and cooled to 0°. This solution was added to a solution of 15 mg (0.13 mmol) potassium hydride (35% in oil) in 0.5 ml DMF that was washed with hexane and kept under $N_2$. This was stirred at 0° for 30 min., then 12 μl (0.13 mmol) allyl bromide was added. The reaction was stirred for 1 hour, then quenched by adding sat. $NH_4Cl$. This solution was diluted with EtOAc, and organic layer was separated. The aqueous layer was extracted with $CH_2Cl_2$. The organic layers were combined, dried over $MgSO_4$, filtered and concentrated in vacuo. The resulting oil was purified by MPLC on a 20×100 mm silica column by eluting with 10% acetone/$CH_2Cl_2$, then dried under high vacuum. 15 mg of a white solid was recovered from the column. Yield=44%.

EXAMPLE 53

4-Methyl-15β-methoxy-17β-propyloxy-4-aza-5α-androstan-3-one (53)

12 mg of (52) was dissolved in 1 ml MeOH. To this was added 2 mg 10% palladium on carbon and hydrogen gas by balloon. The mixture was stirred at 25° overnight, then the catalyst was removed by filtration and the solvent evaporated in vacuo. The resulting oil was purified by HPLC on a 7.8×300 mm Waters μPorisil column by eluting with 5% isopropanol/hexane at 2.9 ml/min. 7 mg of a colorless oil was recovered from the column. Yield=58%.

EXAMPLE 54

4.15β-Dimethyl-17β-AMINO-4-aza-5α-Androstan-3-one (54)

150 mg (0.47 mmol) of (32), 5 ml EtOH, 116 mg (1.42 mmol) sodium acetate and 98 mg (1.452 mmol) hydroxylamine hydrochloride were combined and stirred at 80° for 6 h. The mixture was allowed to cool to room temperature then diluted with water. The precipitate that formed was collected by filtration, washed with water, then air dried. 120 mg of beige solid 4-methyl-15β-methyl-17-oximino-4-aza-5α-androstan-3-one (65) was recovered Yield=77%.

120 mg of 4-methyl-15β-methyl-17-oximino-4-aza-5α-androstan-3-one was dissolved in 2 ml EtOH. To this was added 10 mg platinum oxide, 0.5 ml acetic acid and hydrogen gas by balloon. The mixture was stirred at 25° overnight, then the catalyst was removed by filtration and the solvent evaporated in vacuo. The resulting oil was purified by MPLC on a 21×300 mm silica column by eluting with a gradient from 0% to 10% (10% ammonium hydroxide/MeOH) in $CH_2Cl_2$. 115 mg of a white solid was recovered from the column. Yield=99%.

EXAMPLE 55

4.15β-Dimethyl-17β-(2,2-Dimethylpropanoylamino)-4-aza-5α-androstan-3-one (55)

50 mg (0.16 mmol) of (54), I ml $CH_2Cl_2$, 39 μl (0.31 mmol) trimethylacetyl chloride, and 25 μl (0.31 mmol) pyridine were combined and stirred at 25° for 6 hrs. At this time, a few drops of MeOH was added to the crude reaction mixture to dissolve the precipitate, and the mixture was directly applied to a 21×300 mm silica column and purified by MPLC by eluting with a gradient from 15 to 50% acetone/$CH_2Cl_2$. 51 mg of a white solid was recovered from the column. Yield=79%,

EXAMPLE 56

4,15β-Dimethyl-17β-iso-pentylcarbonylamino-4-aza-5α-androstane (56)

50 mg (0.16 mmol) of (54), 42 mg (0.31 mmol) 1-hydroxybenzotriazole hydrate, 39 μl 4-methylvaleric acid, and 1 ml THF were combined and stirred for 30 min. at 25°. To this was added 60 mg (0.31 mmol) 1-(3-dimethylaminopropyl)-3-ethylcarbodiimide hydrochloride and the mixture was stirred at 25° overnight. The reaction was diluted with EtOAc and sat. $NaHCO_3$, and the aqueous layer extracted with EtOAc. The organic layers were combined, dried over $MgSO_4$, filtered and concentrated in vacuo. The resulting oil was purified by MPLC on a 21×300 mm silica column by eluting with 25% acetone/$CH_2Cl_2$. 50 mg of a white solid was recovered from the column. Yield=75%.

EXAMPLE 57

4-Aza-16α-Bromo-4,7β-Dimethyl-17-(ethylenedioxy)-5α-androstan-3-one (57)

Preparation of Starting Material

The following teaching is for the preparation of starting material 4-aza-4,7β-dimethyl-5α-androstan-3,17-dione. Additional background information can be found in U.S. patent application Ser. No. 07/886,537, filed May 20, 1992, pending, the entire disclosure of which is incorporated herein by reference.

Synthesis of 3-Acetoxy-Androst-5-en-17β-ol

To a solution of 100 mg. (0.303 mmol) of 3-acetoxy-androst-5-en-17-one, 1, in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vacuum, and the residue extracted with ethyl acetate. The organic layer was washed with aqueous $Na_2CO_3$, brine, dried over sodium sulfate and concentrated to leave a residue of crude title compound. Proton NMR confirmed the assigned structure.

Synthesis of 3-Acetoxy 17β-t-Butyldimethylsilyloxy-Androst-5-ene

To a solution of the androstan-17-ol, from the previous synthesis being 4.5 g (13.55 mmol) in 50 ml. dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added and the mixture further stirred overnight. The mixture was poured into I liter water, the solid filtered and washed with water. The solid was dissolved in ethylacetate, the organic layer washed with brine and dried over sodium sulfate, concentrated to yield the silyl protected 17-ol title compound. The proton NMR confirmed the assigned structure.

Synthesis of 3-Acetoxy-17β-t-Butyl-Dimethylsilyloxy-Androst-5-ene-7-one

To a solution of the TBMS protected 17-ol from the previous synthesis, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/ hexane to yield the title compound. Proton NMR confirmed the assigned structure.

Synthesis of 3,17β-t-Butyl-Dimethylsilyloxy-7-Dihydroxy-7-Methyl-Androst-5-ene To a solution of the product from the previous synthesis, being 440 mg. (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confirmed the assigned structure of the title compound which was used in the next step without further purification.

Synthesis of 17β-t-Butyldimethylsilyloxy-7-methyl-Androst-4,6-dien-3-one

The above Grignard product, 3.5 g. (7.142 mmol) was dissolved in 50 ml toluene/50 ml. cyclohexanone and 20 ml of solvent distilled off under vacuum. To this was added 4.54 g. aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound.

Synthesis of 17β)-t-Butyldimethylsilyloxy-7β-Methyl-Androst-5-en-3-one

To a solution of 370 mg of the product of the previous synthesis, in 5.5 ml ammonia, 1 ml THF, 1 mi. toluene, was added 50 mg. of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen stream. The reaction mixture was diluted with brine, extracted with ethyl acetate. The organic layer was washed with brine, dried and concentrated to yield crude material which was used as such in the next synthesis.

Synthesis of 17β-t-Butyldimethylsilyloxy-7β-Methyl-Androst-4-en-3-one

To a solution of the product of the previous synthesis (432) mg in 4 ml THF was added 150 microliters DBU (1,8-diazabicyclo[5.4,0]undec-7-ene) under nitrogen with stirring. The mixture was refluxed for 1.5 hours, then cooled, diluted with NH4Cl solution. The solvent THF was removed under vacuum and the residue extracted with ethyl acetate. The organic layer was washed with brine, dried and concentrated under reduced pressure to yield crude material. The titled product was purified by chromatography on silica gel using 10% EtOAc/hexane as eluant.

Synthesis of 17β-(t-butyldimethylsilyloxy)-7β-methyl-5-oxo-A-nor-3,5-secoandrostan-3-oic acid To a solution of 884 mg of the product of the previous synthesis in 15 ml. t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml. water. The reaction mixture was heated at 80° C. for 2 hours, cooled, filtered, the residue washed with water, and then the extract was concentrated under vacuum. The extract was acidified with aqueous HCl, extracted with ethyl acetate and the organic layer washed with aqueous NaHSO3, brine, dried and concentrated to yield crude 9. The proton NMR confirmed the assigned structure.

Synthesis of 17β-t-Butyldimethylsilyloxy-4,7β-Dimethyl-4-aza-Androst-5-en-3-one To a solution of the product of the previous synthesis, 840 mg in 5 ml ethylene glycol, was added 1.5 g sodium acetate and 737 mg. methylamine hydrochloride. After stirring the reaction mixture 4 hours at 180° C., the mixture was cooled, diluted with water, extracted with ethyl acetate, dried and concentrated to afford crude title compound. Proton NMR confirmed the assigned structure.

Synthesis of 4,7β-Dimethyl-17β-hydroxy-4-aza-Androst-5-en-3-one

To a solution of 700 mg of the product of the previous example, in 20 ml of acetonitrile at 0° C., was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give, crude title compound which was further purified by preparative chromatography on silica gel using 3:1 chloroform/acetone.

Synthesis of 4,7β-dimethyl-17β-hydroxy-4-aza-androstan-3-one

To a solution of the product of the previous synthesis, being 350 mg in 10 ml acetic acid was added 100 mg platinum dioxide and the resulting mixture was evacuated and flushed with hydrogen. The reaction was shaken overnight at room temperature under 40 Psi hydrogen pressure. The solution was filtered concentrated. The residue was worked up with ethyl acetate, the organic layer was then concentrated under vacuum, diluted with ethyl acetate, washed with aqueous NaH- CO₃, brine, dried, concentrated to yield the title compound. Mass Spec: 320 (M+1).

Synthesis of 4,7β-dimethyl-4-aza-5α-androstan-3,17-dione

The product of the previous synthesis, 1.013 g (3.176 mmol) was placed with 6 ml methylene chloride into a dry flask. Powdered molecular 4A sieves, 1.6 g, and 0.558 g (4.76 mmol) of N-methylmorpholine-N-oxide (NMO) and then tetrapropylammonium perruthenate (TPAP), 55 mg (0.159 mmol) were added. The reaction was stirred for 2 hours, diluted with 150 ml ethyl acetate and filtered. The filtrate was evaporated to dryness to yield crude produce which was recrystallized from EtOAc to yield pure product, mp 135°–138° C.

Calc'd for $C_{20}H_{31}NO_2$, mw = 317.48: Calcd: C, 75.67; H, 9.84; N, 4.41; Found: C, 75.16; H, 10.22; N, 4.13; Mass Spec. 318 (M+1).

To a solution of the 4-aza-4,7β-dimethyl-5α-androstan-3,17-dione product of the previous synthesis (1.0 g, 3.15 mmol) in 1:1 ethylene glycol-1,4-dioxane (10 mL) was added copper (11) bromide (3.5 g, 15.7 mmol). The dark red reaction mixture was stirred for 5 hours at 80° C. under a nitrogen atmosphere. The mixture was allowed to cool to room temperature, diluted with a large volume of methylene chloride, washed with water (2×), washed with saturated aqueous sodium chloride solution, dried over sodium sulfate, filtered, evaporated, and dried under high vacuum to afford the desired product in essentially quantitative yield. The material was used without further purification in the subsequent transformation.

EXAMPLE 58

4.7β-Dimethyl-1.7-(ethylenedioxy)-4-aza-5α-androstan-15-ene-3-one (58)

To a solution of 16α-bromo-4,7β-dimethyl-17-(ethylenedioxy)-4-aza-5α-androstan-3-one (1.20 g, 2.72 mmol) in methyl sulfoxide (25 mL) was added potassium tert-butoxide (0.79 g, 7.04 mmol). The reaction, which immediately turned dark red, was stirred for 2 hours at 50° C. under a nitrogen atmosphere. The mixture was allowed to cool to room temperature, diluted with methylene chloride, washed with water, washed with saturated sodium chloride solution, dried. (sodium sulfate), and evaporated. The crude product was purified by flash silica gel chromatography using 15% acetone/methylene chloride as an eluant. Yield=40-0rag (41%).

EXAMPLE 59

4.7β-Dimethyl-4-aza-5α-androstan-15-ene-3,17-dione (59)

A solution of 4,7β-dimethyl-17-(ethylenedioxy)4-aza-5α-androstan-15-ene-3-one (0.35 g, 0.97 mmol) in acetone (35 mL) was stirred with saturated aqueous tartaric acid (7 mL) overnight at room temperature. The reaction mixture was concentrated, partitioned between methylene chloride and water, the organic layer washed with saturated aqueous sodium hydrogen carbonate solution, dried over sodium sulfate, filtered, and evaporated. The crude product was purified by means of flash silica gel chromatography using 35% acetone/methylene chloride as the eluant. Yield=133 mg (43%).

EXAMPLE 60

4.7β, 15-Trimethyl-4-aza-5α-androstan-3,17-dione (60)

To a mixture of copper (I) iodide (325 mg, 1.71 mmol) in diethyl ether (2.7 mL) cooled to 0° C. was added methyllithium (1.4M solution in diethyl ether) (2.5 mL, 3.5 mmol) with stirring under a nitrogen atmosphere. After stirring for 30 min at 0° C., a solution of 4,7β-dimethyl-4-aza-5α-androstan-15-ene-3,17-dione, ( 131 mg, 0.42 mmol) in tetrahydrofuran (1.1 mL) was added dropwise via syringe. The reaction mixture was then stirred for 3 hours at 0° C. and quenched into a saturated ammonium chloride solution. The mixture was extracted with ethyl acetate (2×), and the combined organic extracts were washed with saturated brine solution, dried over sodium sulfate, filtered and evaporated. The crude product was purified by means of flash silica gel chromatography using 2% methanol/methylene chloride as an eluant. The yield was 56.3 mg (41%). The 400 MHz NMR spectrum of the product indicated an approximately 1:1 diastereoisomeric mixture at the 15-position. The mixture was treated with sodium borohydride as described in the subsequent step.

EXAMPLES 61 AND 62

4.7β,15-Trimethyl-17β-hydroxy-4-aza-5α-androstan-3-one (61, 62)

The mixture obtained from the previous transformation (56 mg, 0.17 mmol) was dissolved in methanol (3 mL), cooled in an ice-bath, and treated with sodium borohydride (20 mg, 0.53 mmol) for 2 hours at ice temperature. The mixture was concentrated, partitioned between methylene chloride and water. The aqueous layer was extracted with methylene chloride, and the combined organic extracts were washed with saturated sodium chloride solution, dried over sodium sulfate, filtered, and evaporated. The diastereoisomeric mixture at the 15-position was resolved by HPLC on a 7.8×300 mm Waters μPorisil column eluting with an isopropanol/hexane gradient (5–10% over 60 min) as the mobile phase. The yield of: (1) more mobile isomer A-16.2 mg (29%); (2) less mobile isomer B-22mg (39%).

EXAMPLE 63

4,7β,15-Trimethyl-17β-allyloxy-4-aza-5α-androstan-3-one (ISOMER A) (63)

To a solution of 4,7β,15-trimethyl-17β-hydroxy-4-aza-5α-androstan-3-one (isomer A from previous transformation (13 mg, 0.039 mmol) in N,N-dimethylformamide (0.5 mL) was added sodium hydride (80% dispersion in mineral oil) (8 mg, 0.27 mmol). The mixture was stirred for 15 min at room temperature, at which time allyl bromide (50 μL, 0.58 mmol). The reaction mixture was stirred overnight at room temperature, diluted with diethyl ether, washed with water, dried over sodium sulfate, filtered, and evaporated. The product was purified by means of flash silica gel chromatography using 1–2% methanol/methylene chloride as an eluant. Yield=10 mg (47%).

EXAMPLE 64

4,7β, 15-Trimethyl-17β-allyloxy-4-aza-5α-androstan-3-one (isomer β) (64)

To a solution of 4,7β,15-trimethyl-17β-hydroxy-4-aza-5α-androstan-3-one (isomer B from previous transformation) (19 mg, 0.057 mmol) in N,N-dimethylformamide (0.5 mL) was added sodium hydride (80% dispersion in mineral oil) (8 mg, 0.27 mmol). The mixture was stirred for 15 min at room temperature, at which time allyl bromide (50 mL, 0.58 mmol). The reaction mixture was stirred overnight at room temperature, diluted with diethyl ether, washed with water, dried (sodium sulfate), and evaporated. The product was purified by means of flash silica gel chromatography using 1–2% methanol/methylene chloride as eluant; yield 11 mg (52%).

NMR data is given in the following tables for the compounds exemplified above. Positions given in the table are with reference to the following generic structural formula:

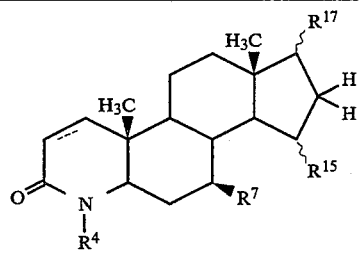

| Example | H$^1$ NMR ($\delta$) | | | Mass spec |
|---|---|---|---|---|
| Number | C$_{18}$ | C$_{19}$ | other | m/e |
| 14 | 0.87 | 0.92 | d, 0.98 | M$^+$ = 305 |
| 15 | 0.94 | 1.02 | d, 1.10 | M$^+$ = 303 |
| 16 | 0.92 | 0.99 | d, 1.01 | M$^+$ = 303 |
| 17 | 0.92 | 0.97 |  | M$^+$ = 317 |
| 18 | 0.83 | 0.89 |  | M$^+$ = 319 |
| 19 | 0.87 | 0.89 | d, 0.99 | M$^+$ = 361 |
| 22 | 0.89 | 0.91 | d, 1.15 | M$^+$ = 317 |
| 23 | 0.76 | 0.88 | d, 1.15 | M$^+$ = 319 |
| 24 | 0.80 | 0.87 | d, 1.00 | M$^+$ = 359 |
| 25 | 0.81 | 0.86 | d, 1.02 | M$^+$ = 303 |
| 26 | 0.87 | 0.87 | d, 1.01 | M$^+$ = 361 |
| 27 | 0.889 | 0.893 | d, 0.98 | M$^+$ = 361) |
| 32 | 0.93 | 1.02 | d, 1.12 | M$^+$ + 1 = 318 |

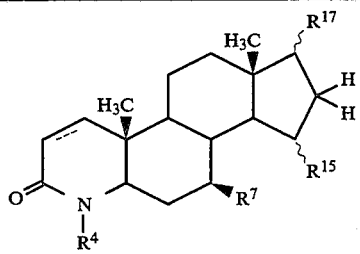

| Ex. | R$^4$ | R$^7$ | R$^{15}$ | R$^{17}$ | |
|---|---|---|---|---|---|
| 14 | H | H | $\beta$-CH$_3$ | $\beta$-OH | |
| 15 | H | H | $\beta$-CH$_3$ | =O | |
| 16 | H | H | $\beta$-CH$_3$ | $\beta$-OH | ($\Delta^1$ double bond) |
| 17 | H | H | $\beta$-C$_2$H$_5$ | =O | |
| 18 | H | H | $\beta$-C$_2$H$_5$ | $\beta$-OH | |
| 19 | H | H | $\beta$-C$_2$H$_5$ | $\beta$-O-n-C$_3$H$_7$ | |
| 22 | CH$_3$ | H | $\alpha$-CH$_3$ | =O | |
| 23 | CH$_3$ | H | $\alpha$-CH$_3$ | $\beta$-OH | |
| 24 | CH$_3$ | H | $\alpha$-CH$_3$ | $\mu$-OCH$_2$CH=CH$_2$ | |
| 25 | CH$_3$ | H | $\alpha$-CH$_3$ | H | |
| 26 | CH$_3$ | H | $\alpha$-CH$_3$ | $\beta$-O-n-C$_3$H$_7$ | |
| 27 | CH$_3$ | H | $\beta$-CH$_3$ | $\beta$-O-n-C$_3$H$_7$ | |
| 32 | CH$_3$ | H | $\beta$-CH$_3$ | =O | |
| 33 | CH$_3$ | H | $\beta$-C$_2$H$_5$ | =O | |
| 34 | CH$_3$ | H | i-C$_3$H$_7$ | =O | (C$_{15}$ stereoisomer A) |
| 35 | CH$_3$ | H | i-C$_3$H$_7$ | =O | (C$_{15}$ stereoisomer B) |
| 36 | CH$_3$ | H | $\beta$-CH$_3$ | $\beta$-OH | |
| 37 | CH$_3$ | H | $\beta$-C$_2$H$_5$ | $\beta$-OH | |
| 39 | CH$_3$ | H | $\beta$-CH$_3$ | $\beta$-OCONH-t-C$_4$H$_9$ | |
| 40 | CH$_3$ | H | $\beta$-CH$_3$ | $\beta$-OCO-t-C$_4$H$_9$ | |
| 41 | CH$_3$ | H | $\beta$-CH$_3$ | H | |
| 43 | CH$_3$ | H | $\beta$-CH$_3$ | $\beta$-CH$_3$ | |
| 46 | CH$_3$ | H | $\beta$-CH$_3$ | $\beta$-(CH$_2$)$_4$CH(CH$_3$)$_2$ | |
| 48 | CH$_3$ | H | $\beta$-CN | =O | |
| 49 | CH$_3$ | H | $\beta$-CN | $\beta$-OH | |
| 50 | CH$_3$ | H | $\beta$-OCH$_3$ | =O | |
| 51 | CH$_3$ | H | $\beta$-OCH$_3$ | $\beta$-OH | |
| 52 | CH$_3$ | H | $\beta$-OCH$_3$ | $\mu$-OCH$_2$CH=CH$_2$ | |
| 53 | CH$_3$ | H | $\beta$-OCH$_3$ | $\beta$-O-n-C$_3$H$_7$ | |
| 54 | CH$_3$ | H | $\beta$-CH$_3$ | $\beta$-NH$_2$ | |
| 55 | CH$_3$ | H | $\beta$-CH$_3$ | $\beta$-NHCO-t-C$_4$H$_9$ | |
| 56 | CH$_3$ | H | $\beta$-CH$_3$ | $\beta$-NHCO-(CH$_2$)$_2$CH(CH$_3$)$_2$ | |
| 61 | CH$_3$ | $\beta$-CH$_3$ | CH$_3$ | $\beta$-OH | (C$_{15}$ stereoisomer A) |
| 62 | CH$_3$ | $\beta$-CH$_3$ | CH$_3$ | $\beta$-OH | (C$_{15}$ stereoisomer B) |
| 63 | CH$_3$ | $\beta$-CH$_3$ | CH$_3$ | $\mu$-OCH$_2$CH=CH$_2$ | (C$_{15}$ stereoisomer A) |
| 64 | CH$_3$ | $\beta$-CH$_3$ | CH$_3$ | $\mu$-OCH$_2$CH=CH$_2$ | (C$_{15}$ stereoisomer B) |

-continued

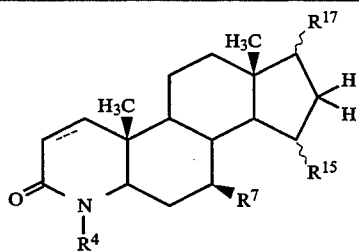

| Example Number | H¹ NMR (δ) $C_{18}$ | $C_{19}$ | other | Mass spec m/e |
|---|---|---|---|---|
| 33 | 0.91 | 0.97 | t, 0.90 | $M^+ + 1 = 331$ |
| 34 | 0.91 | 1.04 | d, 1.08 | $M^+ + 1 = 345$ |
| 35 | 0.89 | 0.93 | d, 0.87 | $M^+ + 1 = 345$ |
| 36 | 0.87 | 0.90 | t, 3.58 | $M^+ + 1 = 320$ |
| 37 | 0.83 | 0.89 | t, 3.60 | $M^+ + 1 = 333$ |
| 39 | 0.88 | 0.88 | t, 4.42 | $M^+ + 1 = 418$ |
| 40 | 0.90 | 0.93 | t, 4.51 | $M^+ + 1 = 403$ |
| 41 | 0.84 | 0.89 | d, 0.94 | $M^+ + 1 = 304$ |
| 43 | 0.67 | 0.89 | d, 0.91 | $M^+ + 1 = 317$ |
| 46 | 0.69 | 0.89 | d, 0.91 | $M^+ + 1 = 402$ |
| 48 | 0.96 | 1.18 | td, 3.23 | $M^+ + 1 = 329$ |
| 49 | 0.93 | 1.01 | t, 3.64 | $M^+ + 1 = 330$ |
| 50 | 0.92 | 1.09 | s, 3.26 | $M^+ + 1 = 333$ |
| 51 | 0.89 | 0.93 | t, 3.58 | $M^+ + 1 = 335$ |
| 52 | 0.89 | 0.97 | t, 3.30 | $M^+ + 1 = 375$ |
| 53 | 0.89 | 0.95 | s, 3.16 | $M^+ + 1 = 378$ |
| 54 | 0.82 | 0.90 | t, 2.67 | $M^+ = 318$ |
| 55 | 0.81 | 0.89 | s, 1.17 | $M^+ = 402$ |
| 56 | 0.82 | 0.89 | q, 3.85 | $M^+ = 416$ |
| 61 | 0.78 | 0.82 | s, 2.91 | ND |
| 62 | 0.87 | 0.89 | s, 2.91 | ND |
| 63 | 0.80 | 0.81 | s, 2.90 | $M^+ = 373$ |
| 64 | 0.87 | 0.90 | s, 2.90 | $M^+ = 373$ |

EXAMPLE 65

Biological Assays

Preparation of Human prostatic and scalp 5a-reductases.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500xg for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay.

The reaction mixture contained in a final volume of 100 μl is: 40 mM buffer (human scalp, potassium phosphate, pH 6.5; human prostatic 5α-reductase, sodium citrate, pH 5.5), 0.3–10 μM¹⁴C-T (or ³H-T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Stint 1 (Radiomatic). Under the conditions described, the production of DHT was linear for at least 25 min. The only steroids observed with the human prostate and scalp preparations were T, DHT and androstanediol.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

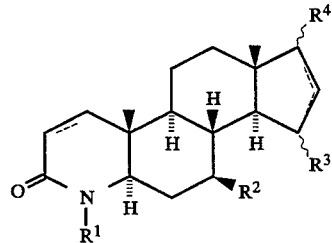

or a pharmaceutically acceptable salt or ester thereof, wherein $R^1$ is selected from the group consisting of hydrogen and $C_{1-10}$ alkyl;

$R^2$ is selected from the group consisting of hydrogen and $C_{1-10}$ alkyl;

$R^3$ is selected from the group consisting of $C_{1-10}$ alkyl, $C_{2-10}$ alkenyl, $C_{1-10}$ alkoxyl, cyano, hydroxyl and triphenylthio-$C_{1-6}$ alkyl;

$R^4$ is either monosubstituted by a substituent selected from the group consisting of keto, spiro-dioxolane and oximino or is disubstituted by hydrogen and $R^5$;

$R^5$ is selected from the group consisting of hydrogen, hydroxyl, Alk-$R^6$, Alk-X-Alk-$R^6$.

$R^6$ is selected from the group consisting of hydrogen, hydroxyl, —CO—$R^7$, —COO—$R^7$, —CO—N-H—$R^7$, —NH—CO—$R^7$ and phenyl;

R[7] is selected from the group consisting of hydrogen, $C_{1-6}$ alkyl, pyridyl and unsubstituted or substituted phenyl where said substituent is halogen, $C_{1-5}$ alkoxyl, $C_{1-5}$ alkylcarbonyl, $C_{1-5}$ alkoxycarbonyl, or $C_{1-5}$ alkylaminocarbonyl;

X is O or NH; and

Alk is $C_{0-10}$ alkyl or $C_{2-10}$ alkenyl with the proviso that when C is O, there is no Alk moiety present.

2. A compound selected from the group consisting of:
4,15β-dimethyl-17β-propyloxy-4-aza-5α-androstan-3-one;
15β-ethyl-17β-hydroxy-4-aza-5α-androstan-3-one;
4-methyl-15β-methoxy-17β-hydroxy-4-aza-5α-androstan-3-one;
4-methyl-15β-cyano-17β-hydroxy-4-aza-5α-androstan-3-one;
15β-ethyl-17-keto-4-aza-5α-androstane-3-one;
4-methyl-15β-methoxy-17β-allyloxy-4-aza-5α-androstan-3-one;
4,15β-dimethyl-17β-amino-4-aza-5α-androstan-3-one;
4,15β-dimethyl-21-isopentyl-4-aza-5α-pregnan-3-one;
4,15β-dimethyl-17β-(2,2-dimethyl-propanoylamino)-4-aza-5α-androstan-3 -one;
4,15β-dimethyl-17β-(4-methyl-n-pentanoylamino)-4-aza-5α-androstane;
4-methyl-15β-methoxy-17β-n-propyloxy-4-aza-5α-aza-androstan-3-one;
4,15β-dimethyl-17β-hydroxy-4-aza-5α-androstan-3-one;
4,15β-dimethyl-17β-(tert-butyl-aminocarbonyloxy)-4-aza-5α-androstan-3-one;
4-methyl-15β-ethyl-4-aza-5α-androstan-3,17-dione;
4,15β,17β-trimethyl-4-aza-5α-androstan-3-one;
4,15β-dimethyl-4-aza-5α-androstan-3,17-dione;
4-methyl-15β-ethyl-17β-hydroxy-4-aza-5α-androstan-3-one;
4-methyl-15α-isopropy14-aza-5α-androstan-3,17-dione;
4-methyl-15β-isopropyl-4-aza-5α-androstan-3,17-dione;
4-aza-15β-ethyl-17β-n-propyloxy-5α-androstan-3-one;
4-aza-15β-methyl-17β-hydroxy-5α-androst-1-en-3-one:
4,15β,-dimethyl-4-aza-5α-androstan-3-one;
4-aza-15β-methyl-17β-hydroxy-5α-androstan-3-one;
4-methyl-15β-methoxy-4-aza-5α-androstan-3, 17-dione;
4, 15β-dimethyl-17β-(2, 2-dimethylpropanoyloxy)-4-aza-5α-androstan-3-one;
4-aza-15β-methyl-5α-androstan-3, 17-dione;
4-methyl-15β-cyano-4-aza-5α-androstane-3, 17-dione;
4,7β,15-trimethyl-17β-hydroxy-4-aza-5α-androstan-3-one;
4,7β,15-trimethyl-17β-allyloxy-4-aza-5α-androstan-3-one;
4,7β,15-trimethyl-4-aza-5α-androstan-3, 17-dione;
4-aza-15β-methyl-17β-hydroxy-5α-androstan-3-one;
4-aza-15βethyl-5α-androstan 3,17-dione;
4-methyl-15α-isopropyl-4-aza-5α-androstane-3, 17-dione; and
4-methyl-15β-isopropyl-4-aza-5α-androstane-3, 17-dione.

3. The compound of claim 1 having the structural formula

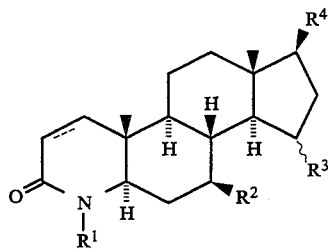

or a pharmaceutically acceptable salt or ester thereof, wherein

R[1] is selected from the group consisting of hydrogen and $C_{1-10}$ alkyl;

R[2] is selected from the group consisting of hydrogen and $C_{1-10}$ alkyl;

R[3] is selected from the group consisting of $C_{1-10}$ alkoxyl, $C_{1-10}$ alkyl and cyano;

R[4] is selected from the group consisting of $C_{1-10}$ alkenyloxyl, $C_{1-10}$ alkoxyl, $C_{1-10}$ alkyl, $C_{1-10}$ alkylcarbamic, $C_{1-10}$ alkylcarbonyloxy, carbonyl, hydroxyl, and —NHR[5]; and R[5] is selected from the group consisting of hydrogen and $C_{1-10}$ alkylcarbonyl.

* * * * *